US009271776B2

(12) United States Patent
Gonzalez-Hernandez

(10) Patent No.: US 9,271,776 B2
(45) Date of Patent: *Mar. 1, 2016

(54) SYSTEM AND METHOD FOR FACILITATING REPAIR AND REATTACHMENT OF COMMINUTED BONE PORTIONS

(71) Applicant: TOBY ORTHOPAEDICS, INC., Miami, FL (US)

(72) Inventor: Eduardo Gonzalez-Hernandez, Miami, FL (US)

(73) Assignee: TOBY ORTHOPAEDICS, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/630,083

(22) Filed: Feb. 24, 2015

(65) Prior Publication Data

US 2015/0164566 A1 Jun. 18, 2015

Related U.S. Application Data

(63) Continuation of application No. 13/253,564, filed on Oct. 5, 2011, now Pat. No. 8,961,573.

(60) Provisional application No. 61/390,082, filed on Oct. 5, 2010, provisional application No. 61/405,438, filed on Oct. 21, 2010, provisional application No. 61/405,793, filed on Oct. 22, 2010.

(51) Int. Cl.
*A61B 17/88* (2006.01)
*A61B 17/86* (2006.01)
(Continued)

(52) U.S. Cl.
CPC ......... *A61B 17/8685* (2013.01); *A61B 17/0401* (2013.01); *A61B 17/7053* (2013.01);
(Continued)

(58) Field of Classification Search
CPC ........... A61B 17/7059; A61B 17/8085; A61B 17/8061; A61B 17/846; A61B 17/0401; A61B 2017/0414
USPC ............... 606/70–71, 74, 280–299, 228–233, 606/138–146
See application file for complete search history.

(56) References Cited

U.S. PATENT DOCUMENTS 1,950,799 A   3/1934 Jones
2,500,370 A   3/1950 McKibbin
(Continued)

FOREIGN PATENT DOCUMENTS

DE   86 28 766 U1   12/1986
DE   89 07 443 U1   9/1989
(Continued)

OTHER PUBLICATIONS

Acumed; ACU-LOC Wrist Plating System; Jul. 2009; 20 pages.
(Continued)

*Primary Examiner* — Anu Ramana
*Assistant Examiner* — Jessica Weiss
(74) *Attorney, Agent, or Firm* — Martin & Ferraro, LLP

(57) ABSTRACT

A fracture fixation system serves in repairing comminuted bone portions of a bone. The fracture fixation system includes a plate having an upper surface, a lower surface opposite the upper surface, one of a screw and a post, and at least one aperture for receiving the one of the screw and the post therethrough. The plate is secured to a main portion of the bone, and the one of the screw and the post is inserted through the at least one aperture through the plate. The portion of the comminuted bone portions is attached to the one of the screw and the post using at least one suture. The one of the screw and the post is rotated to wind the at least one suture therearound to reposition the portion of the comminuted bone portions relative to the main portion of the bone.

20 Claims, 12 Drawing Sheets

(51) Int. Cl.
  *A61B 17/04*  (2006.01)
  *A61B 17/70*  (2006.01)
  *A61B 17/80*  (2006.01)

(52) U.S. Cl.
  CPC ......... *A61B17/809* (2013.01); *A61B 2017/044* (2013.01); *A61B 2017/0409* (2013.01); *A61B 2017/0412* (2013.01); *A61B 2017/0414* (2013.01); *A61B 2017/0417* (2013.01); *A61B 2017/0453* (2013.01); *A61B 2017/0496* (2013.01)

(56) References Cited

U.S. PATENT DOCUMENTS

| | | |
|---|---|---|
| 2,555,291 A | 5/1951 | Poupitch |
| 2,682,265 A | 6/1954 | Collison |
| 2,853,114 A | 9/1958 | Barry |
| 2,875,663 A | 3/1959 | Wieber |
| 3,489,143 A | 1/1970 | Halloran |
| 3,552,389 A | 1/1971 | Allgower et al. |
| 3,579,831 A | 5/1971 | Stevens et al. |
| 3,716,050 A | 2/1973 | Johnston |
| 3,791,380 A | 2/1974 | Dawidowski |
| 3,900,025 A | 8/1975 | Barnes, Jr. |
| 4,263,904 A | 4/1981 | Judet |
| 4,535,768 A | 8/1985 | Hourahane et al. |
| 4,683,878 A | 8/1987 | Carter |
| 4,733,654 A | 3/1988 | Marino |
| 4,776,330 A | 10/1988 | Chapman et al. |
| 4,790,302 A | 12/1988 | Colwill et al. |
| 4,794,919 A | 1/1989 | Nilsson |
| 4,796,612 A | 1/1989 | Reese |
| 4,838,264 A | 6/1989 | Bremer et al. |
| 4,858,602 A | 8/1989 | Seidel et al. |
| 4,870,957 A | 10/1989 | Goble et al. |
| 5,003,969 A | 4/1991 | Azer et al. |
| 5,015,248 A | 5/1991 | Burstein et al. |
| 5,041,113 A | 8/1991 | Biedermann et al. |
| 5,041,114 A | 8/1991 | Chapman et al. |
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,443,516 A | 8/1995 | Albrektsson et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 5,980,575 A | 11/1999 | Albrektsson et al. |
| 6,030,389 A | 2/2000 | Wagner et al. |
| 6,096,040 A | 8/2000 | Esser |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| D449,692 S | 10/2001 | Michelson |
| 6,302,887 B1 | 10/2001 | Spranza et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,776,781 B1 | 8/2004 | Uwaydah |
| 6,863,671 B1 | 3/2005 | Strobel et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 * | 2/2006 | Orbay et al. ................. 606/291 |
| 7,063,701 B2 | 6/2006 | Michelson |
| 7,128,744 B2 | 10/2006 | Weaver et al. |
| D536,453 S | 2/2007 | Young et al. |
| 7,220,246 B2 | 5/2007 | Raulerson et al. |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 | 3/2009 | Kaiser et al. |
| 7,563,263 B2 | 7/2009 | Orbay et al. |
| 7,582,107 B2 | 9/2009 | Trail et al. |
| 7,591,823 B2 | 9/2009 | Tipirneni |
| 7,604,657 B2 | 10/2009 | Orbay et al. |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Watanabe et al. |
| 7,780,710 B2 | 8/2010 | Orbay et al. |
| 7,896,886 B2 | 3/2011 | Orbay et al. |
| 7,909,859 B2 | 3/2011 | Mosca et al. |
| 7,914,532 B2 | 3/2011 | Shaver et al. |
| 7,927,341 B2 | 4/2011 | Orbay et al. |
| 7,938,850 B2 | 5/2011 | Orbay et al. |
| 7,951,176 B2 | 5/2011 | Grady et al. |
| 7,951,178 B2 | 5/2011 | Jensen |
| 7,955,364 B2 | 6/2011 | Ziolo et al. |
| D643,121 S | 8/2011 | Milford et al. |
| 8,021,402 B2 | 9/2011 | Martin et al. |
| D646,785 S | 10/2011 | Milford |
| 8,062,296 B2 | 11/2011 | Orbay et al. |
| 8,062,367 B2 | 11/2011 | Kirschman |
| 8,100,953 B2 | 1/2012 | White et al. |
| 8,182,485 B1 | 5/2012 | Gonzalez-Hernandez |
| 8,317,842 B2 | 11/2012 | Graham et al. |
| 8,361,075 B2 | 1/2013 | Gonzalez-Hernandez |
| 8,469,999 B2 | 6/2013 | Gonzalez-Hernandez |
| 8,523,902 B2 * | 9/2013 | Heaven et al. ................. 606/232 |
| 8,574,234 B2 | 11/2013 | Gonzalez-Hernandez |
| 8,597,363 B2 | 12/2013 | Liverneaux et al. |

(56) References Cited

U.S. PATENT DOCUMENTS

| | | |
|---|---|---|
| 8,690,916 B2 | 4/2014 | Gonzalez-Hernandez |
| 8,728,126 B2 | 5/2014 | Steffen |
| 8,764,808 B2 | 7/2014 | Gonzalez-Hernandez |
| 8,870,963 B2 | 10/2014 | Gonzalez-Hernandez |
| 8,961,573 B2 | 2/2015 | Gonzalez-Hernandez |
| 2002/0091391 A1 | 7/2002 | Cole et al. |
| 2003/0135212 A1 | 7/2003 | Chow |
| 2003/0135216 A1 | 7/2003 | Sevrain |
| 2003/0208210 A1* | 11/2003 | Dreyfuss et al. ............ 606/144 |
| 2004/0097939 A1 | 5/2004 | Bonutti |
| 2004/0193278 A1 | 9/2004 | Maroney et al. |
| 2004/0210220 A1 | 10/2004 | Tornier |
| 2005/0004574 A1 | 1/2005 | Muckter |
| 2005/0015089 A1 | 1/2005 | Young et al. |
| 2005/0021033 A1 | 1/2005 | Zeiler et al. |
| 2005/0038513 A1 | 2/2005 | Michelson |
| 2005/0085819 A1 | 4/2005 | Ellis et al. |
| 2005/0182405 A1 | 8/2005 | Orbay et al. |
| 2005/0240187 A1 | 10/2005 | Huebner et al. |
| 2005/0267476 A1 | 12/2005 | Chervitz et al. |
| 2005/0288681 A1 | 12/2005 | Klotz et al. |
| 2006/0015072 A1 | 1/2006 | Raulerson |
| 2006/0015101 A1 | 1/2006 | Warburton et al. |
| 2006/0106385 A1 | 5/2006 | Pennig |
| 2006/0161156 A1 | 7/2006 | Orbay |
| 2006/0217722 A1 | 9/2006 | Dutoit et al. |
| 2006/0229623 A1 | 10/2006 | Bonutti et al. |
| 2006/0235400 A1 | 10/2006 | Schneider |
| 2006/0241617 A1 | 10/2006 | Holloway et al. |
| 2006/0264947 A1 | 11/2006 | Orbay et al. |
| 2006/0264956 A1 | 11/2006 | Orbay et al. |
| 2006/0271105 A1* | 11/2006 | Foerster et al. ............ 606/232 |
| 2007/0005074 A1 | 1/2007 | Chudik |
| 2007/0016205 A1 | 1/2007 | Beutter et al. |
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233114 A1 | 10/2007 | Bouman |
| 2007/0233115 A1 | 10/2007 | Sixto et al. |
| 2008/0015593 A1 | 1/2008 | Pfefferle et al. |
| 2008/0045960 A1 | 2/2008 | Bruecker et al. |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0076554 A1 | 3/2009 | Huebner et al. |
| 2009/0105838 A1 | 4/2009 | Russo et al. |
| 2009/0125070 A1 | 5/2009 | Sixto, Jr. et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez et al. |
| 2009/0275987 A1 | 11/2009 | Graham et al. |
| 2009/0275991 A1 | 11/2009 | Medoff |
| 2009/0281577 A1 | 11/2009 | Graham et al. |
| 2009/0281578 A1 | 11/2009 | Spencer |
| 2009/0299369 A1 | 12/2009 | Orbay et al. |
| 2009/0306711 A1* | 12/2009 | Stone et al. ............ 606/232 |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0145339 A1 | 6/2010 | Steffen |
| 2010/0145397 A1 | 6/2010 | Overes et al. |
| 2010/0198258 A1* | 8/2010 | Heaven et al. ............ 606/232 |
| 2010/0217393 A1 | 8/2010 | Theofilos |
| 2010/0262194 A1 | 10/2010 | Wagner et al. |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2011/0160730 A1 | 6/2011 | Schonhardt et al. |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0096629 A1* | 4/2013 | Rollinghoff et al. ............ 606/281 |
| 2013/0116734 A1 | 5/2013 | Gonzalez-Hernandez |
| 2013/0338780 A1 | 12/2013 | Berchoux et al. |
| 2014/0121709 A1 | 5/2014 | Gonzalez-Hernandez |
| 2014/0121779 A1 | 5/2014 | Gonzalez-Hernandez |
| 2014/0172020 A1 | 6/2014 | Gonzalez-Hernandez |
| 2014/0180344 A1 | 6/2014 | Gonzalez-Hernandez |
| 2014/0277177 A1 | 9/2014 | Gonzalez-Hernandez |
| 2015/0045898 A1 | 2/2015 | Gonzalez-Hernandez |

FOREIGN PATENT DOCUMENTS

| | | | |
|---|---|---|---|
| DE | 43 43 117 A1 | 6/1995 | |
| DE | 198 57 279 A1 | 6/2000 | |
| DE | 299 07 161 U1 | 8/2000 | |
| EP | 0 551 588 A1 | 11/1992 | |
| EP | 1 132 052 A2 | 9/2001 | |
| EP | 1 468 655 A2 | 10/2004 | |
| FR | 2 606 268 A1 | 5/1988 | |
| FR | 2 680 673 A1 | 3/1993 | |
| FR | 2 712 173 A1 | 5/1995 | |
| JP | 4-138152 A | 5/1992 | |
| WO | WO 99/38448 A1 | 8/1999 | |
| WO | WO 02/071963 A1 | 9/2002 | |
| WO | WO 2005/037117 A1 | 4/2005 | |
| WO | WO 2008/007194 A2 | 1/2008 | |
| WO | WO 2008/007196 A2 | 1/2008 | |
| WO | PCT/EP2010/059922 | * 7/2010 | ............ A61B 17/80 |
| WO | WO 2012/003884 | 1/2012 | |

OTHER PUBLICATIONS

Acumed; The Mayo Clinic Congruent Elbow Plates (catalog); 2003; 19 pages.

Acumed; The Mayo Clinic Congruent Elbow Plate System (catalog); Apr. 2006; 20 pages.

Christie, J., C.R. Howie and P.C. Armour, Fixation of displaced subcapital femoral fractures. Compression screw fixation versus double divergent pins. *J Bone Joint Surg [Br]* 1988; 70-B: 199-201.

Cross, W.M. et al., "Achieving stable fixation: biomechanical designs for fracture healing," AAOS Now (2008) 3 pages.

Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/article.asp?issn=0022-3859;year=2004;volume=50;issue=2;spage=113;epage=114;aulast=Guha.

Hand Innovations, LLC; DVR Anatomic, Volar Plating System; 2007; 4 pages.

Hussain M., R.N. Natarajan, A.H. Fayyazi, B.R. Braaksma, G.B. Andersson and H.S. An, *Screw angulation affects bone-screw stresses and bone graft load sharing in an anterior cervical corpectomy fusion with a rigid screw-plate construct: a finite element model study*; Spine Journal, vol. 9, Issue 12; Dec. 2009; pp. 1016-1023 (published online Oct. 12, 2009).

Lakatos, R. et al.; "General principles of internal fixation"; eMedicine; Aug. 2006; 51 pages.

"MIS Technique," published by Zimmer®, 1 page, prior to Nov. 19, 2004.

Postak, Paul D.; "Biomechanical Properties of Fixed-Angle Volar Distal Radius Plates Under Dynamic Loading;" 2007; 6 pages.

(56) References Cited

OTHER PUBLICATIONS

Robert, III, K.Q., R. Chandler, R,V, Barratta, K.A. Thomas and M.B. Harris, The effect of divergent screw placement on the initial strength of plate-to-bone fixation. *J Trauma*. Dec. 2003;55(6):1139-44.

Synthes, "Large Fragment LCP Instrument and Implant Set;" technique guide; 2003; 31 pages.

Synthes; 3.5 mm LCP Periarticular Proximal Humerus Plate; Apr. 2010; 22 pages.

Synthes; Locking Compression Plate (LCP) System (brochure); 2003; 6 pages.

Synthes, "Locking Compression Plate (LCP) System. Locking screw technology and conventional plating in one system;" 2003; 6 pages.

Synthes; Locking Compression Plate (LCP) System (brochure); Jan. 2007; 6 pages.

Synthes; Modular Mini Fragment LCP System (brochure); 2007; 12 pages.

Synthes; Small Fragment Locking Compression Plate (LCP) System (brochure); 2002; 43 pages.

Written Opinion of the International Searching Authority; International Application No. PCT/US2009/036211; Sep. 23, 2010; 8 pages.

"Zimmer® Universal Locking System," The Journal of Bone and Joint Surgery, vol. 89, No. 7, Jul. 2007, 1 page.

Zimmer, Inc. "Zimmer® Universal Locking System," brochure (2006), 4 pages.

Zimmer, Inc.; "Zimmer Universal Locking System;" brochure; 2009, 2 pages.

Zimmer, Inc. "Zimmer Holdings to Launch Innovative Locking Plate System at Orthopaedic Trauma Association Meeting," Sep. 14, 2006; 3 pages.

Zimmer, Inc.; "Zimmer Small Fragment Universal Locking System;" Surgical Technique; 2010; 16 pages.

Zimmer; Zimmer Periarticular Plating System-Low-Profile Fixation (catalog); 2003; 8 pages.

\* cited by examiner

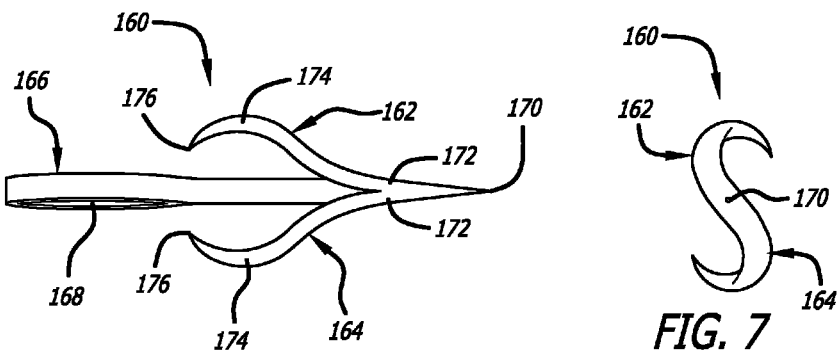
FIG. 6
FIG. 7
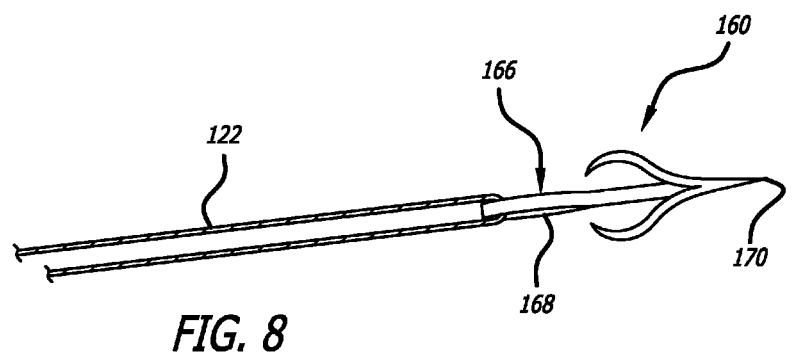
FIG. 8
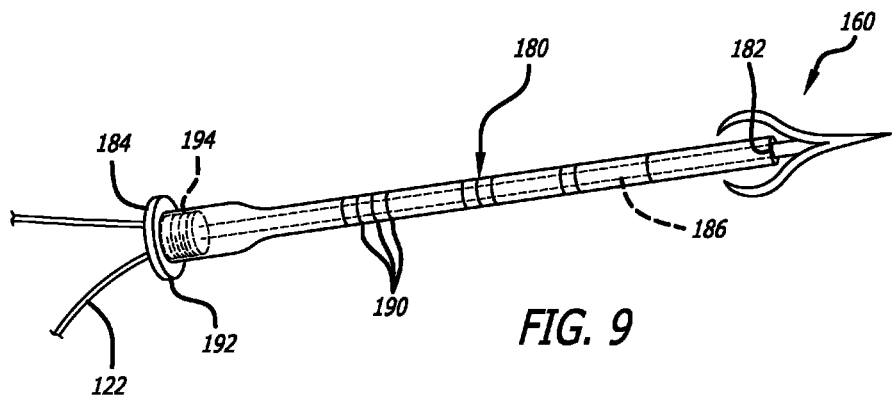
FIG. 9

SYSTEM AND METHOD FOR FACILITATING REPAIR AND REATTACHMENT OF COMMINUTED BONE PORTIONS

RELATED APPLICATIONS

This application is a continuation of U.S. application Ser. No. 13/253,564, filed Oct. 5, 2011 (now U.S. Pat. No. 8,961, 573), which claims the benefit of U.S. Provisional Application No. 61/390,082, filed Oct. 5, 2010, entitled "System and Method for Facilitating Repair and Reattachment of Comminuted Bone Portions"; U.S. Provisional Application No. 61/405,438, filed Oct. 21, 2010, entitled "Bone Plate with Soft Tissue Attachment Structure"; and U.S. Provisional Application No. 61/405,793, filed Oct. 22, 2010, entitled "Suture Anchor and Method of Use Associated Therewith"; all of which are hereby incorporated by reference herein.

BACKGROUND

1. Field of the Invention

The present invention is generally related to a medical device and method for use thereof for facilitating repair of comminuted bone fractures. In particular, the present invention is related to a fracture fixation system and method for use thereof to aid in the repair of comminuted periarticular fractures. More specifically, the present invention relates to a fracture fixation system and method for use thereof for aligning and stabilizing comminuted bone portions and associated soft tissues adjacent joints to facilitating proper healing.

2. Description of the Prior Art

A comminuted periarticular fracture is a fracture in which bone is broken, splintered, or crushed into a number of pieces adjacent a joint. In comminuted periarticular fractures there is a great need for fixation of important bony fragments (or comminuted bone portions) that have relevant blood supply to facilitate fracture healing. Such comminuted bone portions may have tendons or ligaments attached thereto which also need to heal in place in order to restore function to the joint in question. For example, as in fractures of the lesser tuberosity, frequently there are avulsed tendons that are attached to the comminuted bone portions.

A wide variety of devices have been developed for the support and treatment of comminuted periarticular fractures. Existing solutions have ranged from simplistic measures, such as bone support plates, structural rods, and other single-function prosthetic devices, to more elaborate mechanisms involving a complex arrangement of different components. Despite advances in the devices for the support and treatment of comminuted periarticular fractures, increasing the alignment and stability of the comminuted bone portions and associated tissue can aid in restoring function to the damaged joint.

Therefore, there is a need for a fracture fixation system to aid repair and reattachment of comminuted bone portions and associated tissue by facilitating increased alignment and stability of the comminuted bone portions and associated tissue. Such a fracture fixation system can increase the alignment and stability of the comminuted bone portions and associated tissue by providing an ideal mechanical advantage for drawing multiple comminuted bone portions together to form a solid construct to facilitate healing thereof, and to facilitate attachment of the associated tissue.

For example, the fracture fixation systems disclosed herein can be used to fix portions of a comminuted humeral head relative to a humeral shaft portion (FIGS. 1 and 2). In doing so, the comminuted humeral head portions (whether they contain important blood supply, or important tendon or ligament attachments) can be fixed to the site of their avulsion or prior attachment. As such, using the fracture fixation systems disclosed herein, the comminuted humeral head portions can be drawn together to form a solid construct to facilitate healing thereof, and to facilitate attachment of the associated tissue. The fracture fixation systems disclosed herein include improvements to the inventions described in U.S. Provisional Application Nos. 60/523,960; 60/541,540; and 60/552,632; and U.S. application Ser. No. 10/993,723, which are incorporated herein by reference.

SUMMARY OF THE INVENTION

The present invention in one preferred embodiment includes a method of repairing a comminuted humeral head of a humeral bone, the method including the following acts. A plate having an upper surface, a lower surface opposite the upper surface, and at least one aperture for receiving one of a screw and a post therethrough is provided. The plate is secured to a portion of a humeral shaft of the humeral bone. The one of the screw and the post is inserted through the at least one aperture through the plate. The portion of the comminuted humeral head is attached to the one of the screw and the post using at least one suture. The one of the screw and the post is rotated to wind the at least one suture around the one of the screw and the post, where the winding of the at least one suture draws the portion of the comminuted humeral head closer to the one of the screw and the post to position the portion of the comminuted humeral head relative to the portion of the humeral shaft.

In another preferred embodiment, the present invention includes a method of repairing a comminuted humeral head of a humeral bone, the method including the following acts. A plate having an upper surface, a lower surface opposite the upper surface, at least one fin extending outwardly from the lower surface of the plate, and at least one aperture for receiving one of a screw and a post therethrough is provided. The plate is secured to a portion of a humeral shaft of the humeral bone. The one of the screw and the post is inserted through the at least one aperture through the plate. The portion of the comminuted humeral head is attached to the one of the screw and the post using at least one suture, where the at least one suture is received through an aperture formed in the at least one fin and through a hole formed in the one of the screw and the post. The one of the screw and the post is rotated to wind the at least one suture around the one of the screw and the post, where the winding of the at least one suture draws the portion of the comminuted humeral head closer to the at least one fin and to the one of the screw and the post, and where the at least one fin is positioned between the portion of the comminuted humeral head and the one of the screw and the post.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings:

FIG. 6 is a side elevational view of a suture anchor for use as part of the fracture fixation systems disclosed herein;

FIG. 7 is a front elevational view of the suture anchor depicted in FIG. 6;

FIG. 8 is a perspective view of the suture anchor depicted in FIGS. 6 and 7 in combination with a suture;

FIG. 9 is a perspective view of the suture anchor depicted in FIGS. 6-8 in combination with the suture and a hollow needle;

DETAILED DESCRIPTION OF THE PREFERRED EMBODIMENT

The fracture fixation systems of the present invention depicted in the accompanying drawings are used to facilitate repair and reattachment of comminuted bone portions and associated tissue. In doing so, the fracture fixation systems of the present invention serve in aligning and stabilizing comminuted bone portions and associated tissue adjacent joints to facilitate proper healing.

Figure 1:
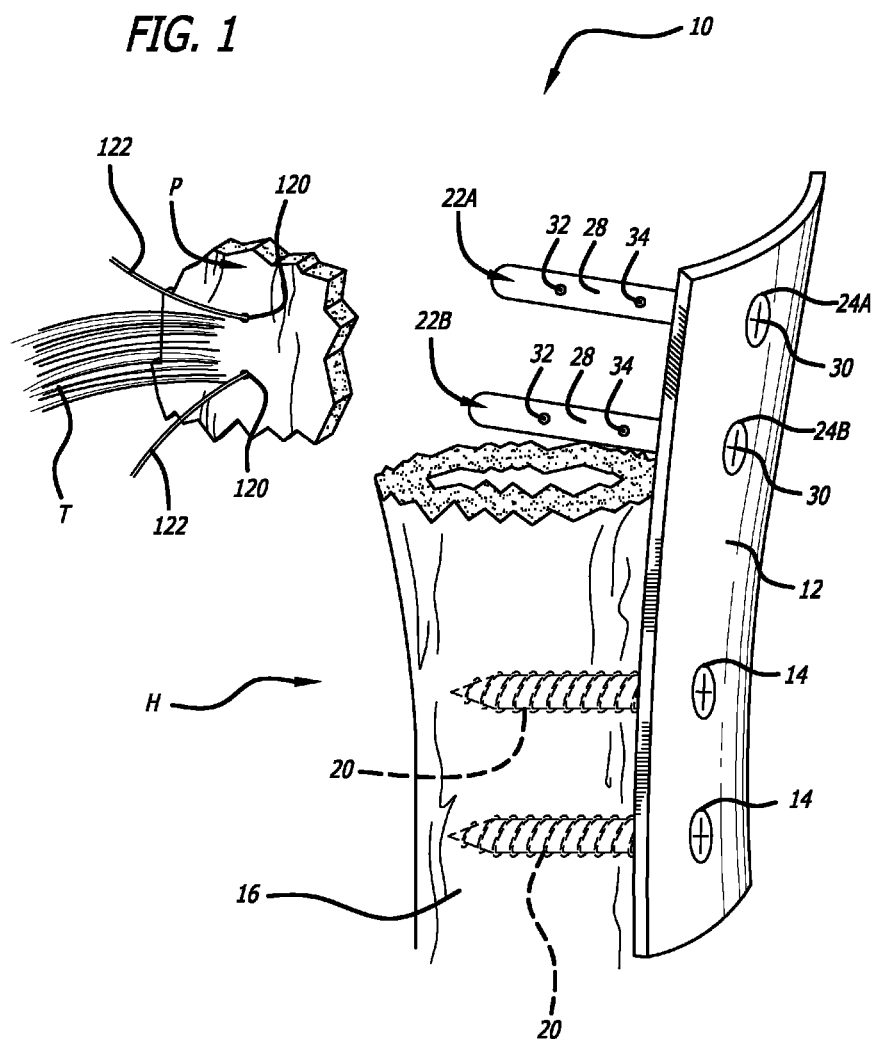
FIG. 1 is a perspective view of a first embodiment of a fracture fixation system positioned with respect to a comminuted portion of a humeral head and a humeral shaft portion.
Figure 2:
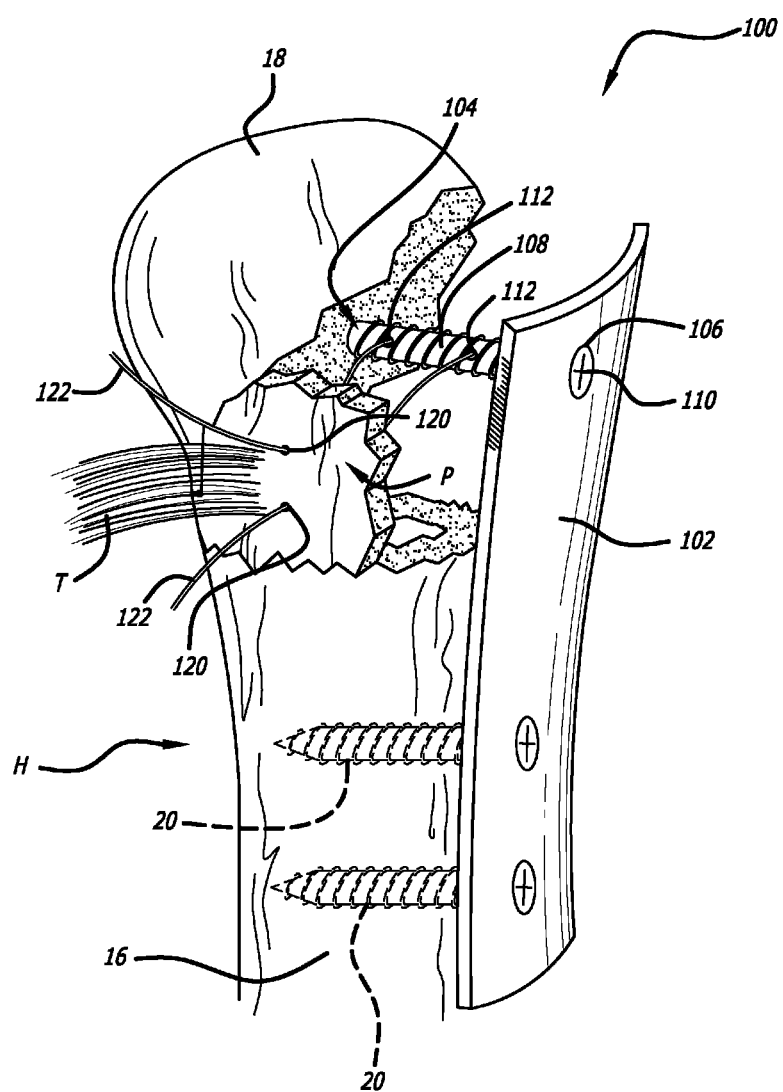
FIG. 2 is a perspective view of a second embodiment of the fracture fixation system positioned with respect to comminuted portions of the humeral head and the humeral shaft portion.

A first illustrative embodiment of the fracture fixation system is generally indicated by the numeral 10 in FIG. 1, and a second illustrative embodiment of the fracture fixation system is generally indicated by the numeral 100 in FIG. 2. Fracture fixation systems 10 and 100 and the other illustrative embodiments of the fraction fixation system described herein can be used to aid repair and reattachment of a comminuted humeral head and the tissue associated therewith. In doing so, components of the fracture fixation systems described herein can be used to provide attachment points for one or more portions (referred hereinafter singularly as portion P) of the comminuted humeral head. In doing so, fracture fixation systems described herein also can be used to provide attachment points for reattachment of associated tissue T (such as tendons and ligaments) associated with comminuted humeral head portion P. Thus, when describing attachment of comminuted humeral head portion P below, it will be assumed that associated tissue T also can be reattached to comminuted humeral head portion P using the components of the fracture fixation systems described herein.

Depending on the degree of comminution of the bone, either of fracture fixation systems 10 or 100 can be used. For example, fracture fixation system 10 includes two attachment structures to accommodate a higher level of comminution, and fracture fixation system 100 includes one attachment structure to accommodate a lower level of comminution. However, although not shown herein, the number of attachment structures included in fracture fixation systems 10 and 100 can be varied to accommodate higher or lower levels of comminution. For example, fracture fixation system 10 can be provided with one of the attachment structures depicted in FIG. 1, fracture fixation system 100 can be provided with two of the attachment structures depicted in FIG. 2, or both fracture fixation systems 10 and 100 can be provided with three or more of the attachment structures associated therewith. Furthermore, the attachment structures associated with FIGS. 1 and 2 can be interchangeable and be used together with one another.

As discussed above, fracture fixation systems 10 and 100 are discussed in association with a humeral bone H, in particular the comminuted humeral head. More specifically, in FIGS. 1 and 2, fracture fixation systems 10 and 100 are depicted to illustrate fixation of the lesser tuberosity in fractures of the proximal humerus. However, fracture fixation systems 10 and 100, as well as the other illustrative embodiments of the fracture fixation system disclosed herein, are not so limited and can be utilized with other comminuted bone portions and the tissue associated therewith.

Fracture fixation system 10 of FIG. 1 includes an external plate portion 12 having screw apertures 14. External plate portion 12 is secured to humeral bone H. For example, as depicted in FIG. 1, external plate portion 12 is attached to the exterior surfaces of humeral shaft portion 16 of humeral bone H. Furthermore, depending on whether additional portions of the comminuted humeral head remain attached to humeral shaft portion 16, external plate portion 12 can also be attached to the exterior surfaces thereof.

Screw openings (not shown) that respectively register with screw apertures 14 in external plate portion 12 are provided in humeral shaft portion 16, and if available, the additional portions of the comminuted humeral head. The screw openings in humeral shaft portion 16, for example, are formed in generally transverse relationships with respect to the longitudinal axis of humeral shaft portion 16.

To attach external plate portion 12 to humeral bone H, plate screws 20 are respectively received in screw apertures 14 of external plate portion 12 and the screw openings in humeral shaft portion 16, and, if available, the additional portions of the comminuted humeral head. If necessary, plate screws 20 can be respectively locked to screw apertures 14 by, for example, providing cooperating screw threads (not shown) on the exteriors of plate screws 20 and on the interior surfaces of screw apertures 14.

As depicted in FIG. 1, two attachment structures in the form of scaffold building posts 22A, 22B are received in scaffold building post apertures 24A, 24B, respectively, provided in external plate portion 12. Scaffold building posts 22A, 22B each include a shaft 28 and a head 30. Shaft 28 can be provided with threads (not shown) to facilitate attachment thereof to larger portions of the comminuted humeral head. Furthermore, if necessary, scaffold building posts 22A, 22B can be locked to scaffold building post apertures 24A, 24B, respectively. For example, this may be accomplished by providing complementary threads (not shown) on the exterior of head 30 and on the interior of scaffold building post apertures 24A, 24B.

Scaffold building posts 22A, 22B with or without fenestrations can be used to facilitate attachment of comminuted humeral head portion P thereto. If no fenestrations are provided, sutures, wires, or cables can be wrapped around scaffold building posts 22A, 22B to facilitate attachment of comminuted humeral head portion P thereto.

Alternatively, one or more bracing apertures 32 and 34 can extend transversely through shafts 28 of each of scaffold building posts 22A, 22B. Bracing apertures 32 and 34 may be disposed in generally perpendicular relationship or at any desired angle with respect to the longitudinal axes of shafts 28. Bracing apertures 32 and 34, for example, can be disposed in generally perpendicular or transverse relationships with respect to each other. As discussed below, bracing apertures 32 and 34 are used for anchoring comminuted humeral head portion P with respect to the remainder of humeral bone H.

Fracture fixation system 100 of FIG. 2 includes an external plate portion 102. Like external plate portion 12 of fracture fixation system 10, external plate portion 102 is secured to humeral bone H. Fracture fixation system 100, but for the use of a single different attachment structure, has a similar configuration and is used in similar fashion to fracture fixation system 10 (FIG. 1). Thus, where applicable, identical element numbers are applied to elements shared by fracture fixation systems 10 and 100 in FIGS. 1 and 2.

As depicted in FIG. 2, one attachment structure in the form of a scaffold building screw 104 is received in a scaffold building screw aperture 106 provided in external plate portion 102. Scaffold building screw 104 is similar to scaffold building posts 22A, 22B, and includes a shaft 108 and a head 110. If necessary, scaffold building screw 104 can be locked to scaffold building screw aperture 106. For example, this may be accomplished providing complementary threads (not shown) on the exterior of head 110 and on the interior of scaffold building screw aperture 106.

Shaft 108 is threaded to facilitate attachment to a humeral head portion 18. As depicted in FIG. 2, humeral head portion 18 is a large fragment of the comminuted humeral head, and includes an opening (not shown) provided therein for receiving a portion of scaffold building screw 104. When scaffold building screw 104 is received in scaffold building screw aperture 106 and the scaffold building screw opening in humeral head portion 18, scaffold building screw 104 secures humeral head portion 18 in relation to external plate portion 102 and humeral shaft portion 16.

Like scaffold building posts 22A, 22B, scaffold building screw 104 with or without fenestrations can be used to facilitate attachment of the comminuted humeral head portion P thereto. If no fenestrations are provided, sutures, wires, or cables can be wrapped around scaffold building screw 104 to facilitate attachment of comminuted humeral head portion P thereto.

Alternatively, one or more bracing apertures 112 can extend transversely through shaft 108 of scaffold building screw 104. Bracing apertures 112 may be disposed in generally perpendicular relationship or at any desired angle with respect to the longitudinal axis of shaft 108. As discussed below, bracing apertures 112 are used for anchoring comminuted humeral head portion P with respect to the remainder of humeral bone H.

When using fracture fixation systems 10 and 100, comminuted humeral head portion P is ultimately attached to scaffold building posts 22A, 22B and/or scaffold building screw 104. The point of anchorage and line of pull afforded by scaffold building posts 22A, 22B and scaffold building screw 104 are otherwise unobtainable. The illustrative embodiments of the fracture fixation system disclosed herein provide an ideal mechanical advantage for drawing multiple bone portions together to form a solid construct to facilitate healing thereof.

To facilitate attachment of comminuted humeral head portion P to scaffold building posts 22A, 22B and/or scaffold building screw 104, holes 120 can be provided in comminuted humeral head portion P. One or more of sutures 122 (referred hereinafter singularly) can be passed through holes 120 and inserted into one of bracing apertures 32, 34, and 112 to draw comminuted humeral head portion P toward the corresponding one of scaffold building posts 22A, 22B, and scaffold building screw 104. As such, using the leverage provided by scaffold building posts 22A, 22B and/or scaffold building screw 104, comminuted humeral head portion P can be positioned relative thereto, and hence, relative to the surrounding bone portions.

Thereafter, suture 122 (attached to comminuted humeral head portion P) can be attached to the corresponding one of scaffold building posts 22A, 22B and scaffold building screw 104 to secure comminuted humeral head portion P relative thereto and to surrounding bone portions. For example, if suture 122 is inserted into bracing aperture 112, suture 122 can be tied to the portions of scaffold building screw 104 surrounding bracing aperture 112 to attach comminuted humeral head portion P to scaffold building screw 104.

Figure 3A:
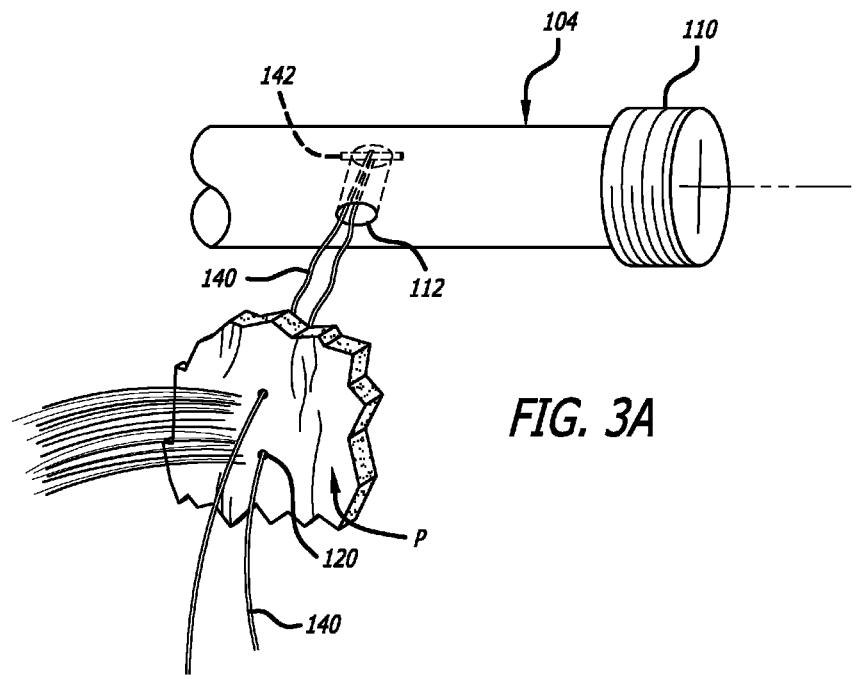
FIG. 3A is a perspective view of a scaffold building screw of the fracture fixation system depicted in FIG. 2 illustrating a method for attaching sutures thereto.
Figure 3B:
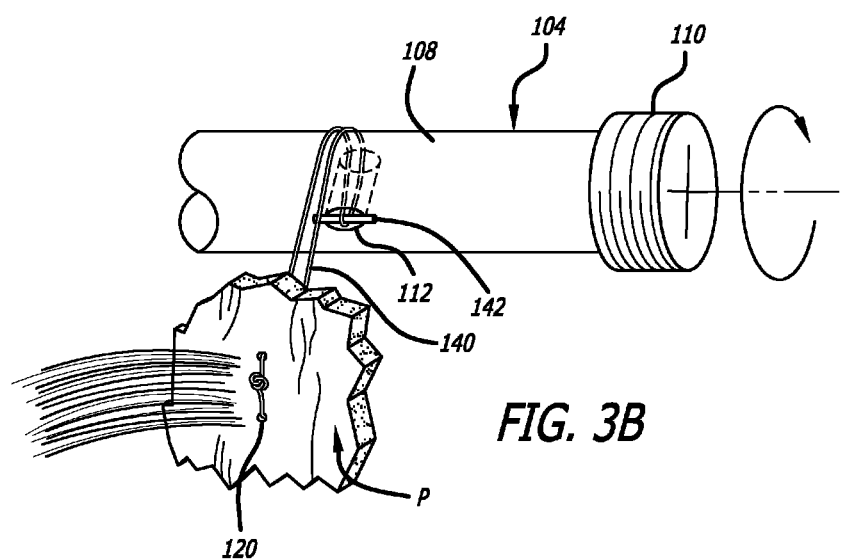
FIG. 3B is a perspective view of the scaffold building screw depicted in FIG. 3A after the scaffold building screw of the fracture fixation system depicted in FIG. 2 has been rotated.

Alternatively, suture anchors (such as anchor portion 142 of a modified suture 140 discussed below) can be provided to secure comminuted humeral head portion P relative to scaffold building posts 22A, 22B and/or scaffold building screw 104. Modified suture 140 can be attached to comminuted humeral head portion P, and, as depicted in FIGS. 3A and 3B, for example, anchor portion 142 thereof can be inserted completely through bracing aperture 112 of scaffold building screw 104. Shaft 108 of scaffold building screw 104 is not depicted with threads in FIGS. 3A and 3B to better show the interaction between modified suture 140 and scaffold building screw 104. As depicted in FIGS. 3A and 3B, anchor portion 142 catches on the portions of scaffold building screw 104 adjacent the exit to bracing aperture 112. In doing so, anchor portion 142 prevents withdrawal of modified suture 140 from bracing aperture 112, and hence, attaches comminuted humeral head portion P to scaffold building screw 104.

With comminuted humeral head portion P attached to one of scaffold building posts 22A, 22B, and scaffold building screw 104 using suture 122 and/or modified suture 140, the one of scaffold building posts 22A, 22B and scaffold building screw 104 can be rotated to further strengthen the attachment therebetween. That is, rotation of the one of scaffold building posts 22A, 22B, and scaffold building screw 104 causes suture 122 and/or modified suture 140 to wind therearound. Such winding draws comminuted humeral head portion P closer to the one of scaffold building posts 22A, 22B, and scaffold building screw 104. For example, as depicted in FIGS. 3A and 3B, after anchor portion 142 is inserted through bracing aperture 112 to attach comminuted humeral head portion P to scaffold building screw 104, scaffold building screw 104 can be rotated to reposition bracing aperture 112 rotationally and wind modified suture 140 around shaft 108. In doing so, comminuted humeral head portion P is drawn toward scaffold building screw 104, and the attachment of comminuted humeral head portion P and scaffold building screw 104 is strengthened. Moreover, rotation of scaffold building screw 104 and attendant repositioning of bracing aperture 112 also provides another position for attachment of additional sutures thereto.

To maintain attachment of scaffold building posts 22A, 22B and scaffold building screw 104 relative to respective plate portions 12 and 102 during rotation, the above-discussed complementary threads (not shown) are provided on heads 30 of scaffold building posts 22A, 22B, and provided on head 110 of scaffold building screw 104. The threads on heads 30 interact with complementary threads provided in scaffold building post apertures 24A, 24B, and threads on head 110 interact with complementary threads provided in scaffold building screw aperture 106. The interaction of the threads maintains attachment of scaffold building posts 22A, 22B to plate portion 12 during rotation thereof, maintains attachment of scaffold building screw 104 to plate portion 102 during rotation thereof, and serves in preventing unwanted axial movement of scaffold building posts 22A, 22B and scaffold building screw 104 relative to their respective apertures. As such, suture 112 and/or modified suture 140 can be wound around scaffold building posts 22A, 22B and/or scaffold building screw 104 without fear of detachment from respective plate portions 12 and 102.

Furthermore, in addition to the complementary threads for preventing unwanted axial movement, fracture fixation systems 10 and 100 can also include ratcheting mechanisms for preventing unwanted rotational movement of scaffold building posts 22A, 22B and scaffold building screw 104 relative to their respective apertures. For example, heads 30 (of scaffold building posts 22A, 22B) and head 110 (of scaffold building screw 104) can each include teeth (not shown) surrounding an exterior portion thereof. The teeth provided on heads 30 can interact with a latch (not shown) or complementary teeth (not shown) provided on exterior plate portion 12 and/or in scaffold building post apertures 24A, 24B; and the teeth provided on head 110 can interact with a latch (not shown) or complementary teeth (not shown) provided on exterior plate portion 102 and/or in scaffold building screw aperture 106. The teeth on heads 30 and 110, and the corresponding latch or complementary teeth can interact to prevent unwanted rotational movement of scaffold building posts 22A, 22B and scaffold building screw 104 relative to their respective apertures. As such, such an interaction can serve in preventing scaffold building posts 22A, 22B and scaffold building screw 104 from backing out of their respective apertures.

In addition to suture 122, suture anchors (such as anchor portion 142 of modified suture 140 discussed above) can be employed for securing comminuted humeral head portion P relative to scaffold building posts 22A, 22B and scaffold building screw 104. For example, various suture anchors can be used with suture 122, wires, and/or or cables to secure comminuted humeral head portion P. The various suture anchors described herein can be used as part of fracture fixation systems 10 and 100 and the other illustrative embodiments described herein.

Figure 4:
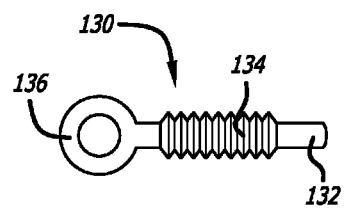
FIG. 4 is a side elevational view of an anchor post for use with the fracture fixation systems disclosed herein.

One or more suture anchors such as an anchor post 130 depicted in FIG. 4 can be used to secure comminuted humeral head portion P in position relative to scaffold building posts 22A, 22B and scaffold building screw 104. Anchor post 130 includes an end portion 132, a threaded shaft portion 134, and an eyelet portion 136. Anchor post 130 can be attached to scaffold building posts 22A, 22B using bracing apertures 32 and 34, and scaffold building screw 104 using bracing aperture 112. To facilitate attachment, threaded shaft portion 134 can engage complementary threads provided in bracing apertures 32, 34, and 112. Thereafter, suture 122 can be received through eyelet portion 136 to secure comminuted humeral head portion P relative to scaffold building posts 22A, 22B and scaffold building screw 104.

Figure 5:
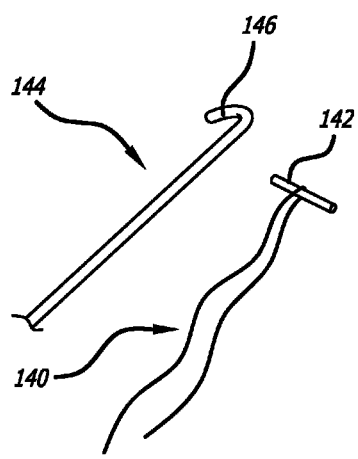
FIG. 5 is a perspective view of a modified suture and a malleable wire for use with the fracture fixation systems disclosed herein.

Furthermore, suture anchors in the form of anchor portion 142 of modified suture 140 and a malleable wire 144 are depicted in FIG. 5. As depicted in FIG. 5, modified suture 140 includes anchor portion 142 at an end thereof, and malleable wire 144 includes a hook 146 at an end thereof. Like modified suture 140, malleable wire 144 can also be used to secure comminuted humeral head portion P in position relative to scaffold building posts 22A, 22B and scaffold building screw 104. In either instance, modified suture 140 and malleable wire 144 are inserted through holes 120 of comminuted humeral head portion P into bracing apertures 32, 34, and 112.

Anchor portion 142 and hook 146 are inserted first through holes 120 and entrances to bracing apertures 32, 34, and 112. When received completely through bracing apertures 32, 34, and 112, anchor portion 142 and hook 146 prevent withdrawal of modified suture 140 and malleable wire 144, respectively, from holes 120 and bracing apertures 32, 34, and 112. That is, when modified suture 140 and malleable wire 144 are under tension, anchor portion 142 and hook 146 catch on the portions of building posts 22A, 22B and scaffold building screw 104 adjacent the exits to the corresponding bracing apertures 32, 34, and 112, and in doing so, prevent withdrawal of modified suture 140 and malleable wire 144 bracing apertures 32, 34, and 112.

Because anchor portion 142 prevents withdrawal, modified suture 140 can be tied off to secure comminuted humeral head portion P relative to scaffold building posts 22A, 22B or to scaffold building screw 104; and because hook 146 also prevents withdrawal, malleable wire 144 can be used to pin comminuted humeral head portion P relative to scaffold building posts 22A, 22B or to scaffold building screw 104.

Also, because anchor portion 142 and hook 146 prevent such withdrawal, scaffold building posts 22A, 22B and scaffold building screw 104 can be rotated to wind modified suture 140 (FIGS. 3A and 3B) and malleable wire 146 therearound.

A suture anchor for use with suture 122 is generally indicated by the numeral 160 in FIGS. 6-9. Suture anchor 160 can be used in attaching suture 122 to scaffold building posts 22A, 22B and scaffold building screw 104. In doing so, suture anchor 160 can be used to secure comminuted humeral head portion P in position relative to scaffold building posts 22A, 22B and scaffold building screw 104.

As depicted in FIG. 6, suture anchor 160 is generally harpoon shaped, and includes a first arm portion 162, a second arm portion 164, a body portion 166 (including a slot (or cavity) 168 therethrough), and a distal end (or tip) 170. Tip 170 is used to facilitate penetration of soft tissues and/or bone. Slot 168 is configured to allow suture 122 to be received therethrough. For example, as depicted in FIG. 8, suture 122 is looped around body portion 166 using slot 168. Furthermore, first and second arm portions 162 and 164 can be deformed inwardly toward body portion 166 (i.e., compression) and outwardly away from body portion 166 (i.e., tension).

First and second arm portions 162 and 164 can be moveable with respect to one another, and can be shaped to facilitate entry into and resist removal from soft tissues and/or bone. As such, first and second arm portions 162 and 164 facilitate attachment of suture 122 (that is also attached to suture anchor 160) to the soft tissues and/or bone. For example, both first and second arm portions 162 and 164 include generally straight sections 172 extending rearwardly from tip 170, and curved sections 174 extending rearwardly from straight sections 172. Straight sections 172, as depicted in FIG. 6, are acutely angled with respect to one another. As such, even after compression of first and second arm portions 162 and 164 inwardly toward body portion 166, straight sections 172 serve to gradually wedge apertures (not shown) formed through the soft tissues and/or bone open to permit passage of the remainder of suture anchor 160. Furthermore, as depicted in FIG. 6, curved sections 174 can be arcuately shaped along the length thereof. After penetration of suture anchor 160 through the soft tissues and/or bone, ends 176 of curved sections 174 can grab the soft tissues and/or bone to prevent removal thereof from the apertures in the soft tissues and/or bone.

As depicted in FIG. 7, first and second arm portions 162 and 164 can also be twisted along their lengths. For example, as first and second arm portions 162 and 164 extend rearwardly from tip 170, first and second arm portions 162 and 164 can be twisted in clockwise and/or counterclockwise directions. In FIG. 7, first and second arm portions 162 and 164 are both twisted in clockwise directions.

Suture anchor 160 can be made of a resilient material such as nitinol. As such, suture anchor 160 is biased in the position depicted in FIGS. 6-9. Thus, the "memory" afforded by nitinol allows suture anchor 160 to return to its original shape after deformation thereof. For example, first and second arm portions 162 and 164 can be contracted and expanded, and will return to their original positions with respect to body portion 166 after compression (causing the contraction thereof) or tension (causing the expansion thereof) has been released.

As depicted in FIG. 8, slot 168 of body portion 166 is configured to receive suture 122 therethrough. Suture 122 can be attached to suture anchor 160 using slot 168. For example, suture 122 can be looped around (FIG. 8) or tied to suture anchor 160 using slot 168. Thus, as suture anchor 160 penetrates soft tissues and/or bone, suture 122 is also drawn through the apertures in the soft tissues and/or bone.

To aid penetration of suture anchor 160 through soft tissues and/or bone, a hollow needle 180 (FIG. 9) can be provided. As depicted in FIG. 9, hollow needle 180 includes a distal end 182, a proximal end 184, and a length extending therebetween. Hollow needle 180 includes a passage 186 extending between distal end 182 and proximal end 184, and can be formed from hypodermic tubing. Passage 186 through hollow needle 180 is configured to receive suture anchor 160 and suture 122 attached thereto. As depicted in FIG. 9, suture anchor 160 and suture 122 can be inserted through hollow needle 180 such that suture anchor 160 is positioned adjacent distal end 182 and suture 122 extends outwardly from proximal end 184. During use, the combined suture anchor 160, suture 122, and hollow needle 180 can penetrate soft tissues and/or bone.

The rigidity afforded by hollow needle 180 allows the combined suture anchor 160, suture 122, and hollow needle 180 to penetrate relatively robust soft tissues and/or bone. Once suture anchor 160 extends into or through to the opposite side of the soft tissues and/or bone, hollow needle 180 can be removed from the soft tissues and/or bone. Thereafter, first and second arm portions 162 and 164 prevent removal from the soft tissues and/or bone.

Markings 190 are provided on the exterior of hollow needle 180 to aid in limiting the depth of penetration of hollow needle 180 through the soft tissues and/or bone. Using markings 190, the depth of penetration can be gauged. A shoulder 192 is provided to prevent over-penetration of hollow needle 180. Once in contact with the soft tissues and/or bone, shoulder 192 resists further insertion therethrough. Furthermore, threads 194 are provided on the interior of needle adjacent shoulder 192. Threads 194 allow attachment of hollow needle 180 to another tool (not shown) to facilitate manipulation thereof.

When attached to soft tissues and/or bone, suture anchor 160 (and the portion of suture 122 attached thereto) can be inserted through bracing apertures 32, 34, and 112. Once inserted therein, first and second arm portions 162 and 164 resist withdrawal of suture anchor 160 from bracing apertures 32, 34, and 112. That is, once inserted into an entrance of and completely through the one of bracing apertures 32, 34, and 112, first and second arm portions 162 and 164 serve as catches that interact with portions of the corresponding scaffold building posts 22A, 22B and scaffold building screw 104 adjacent the one of bracing apertures 32, 34, and 112 to prevent withdrawal under tension of suture 122. Thus, suture anchor 160 can serve in attaching suture 122 to scaffold building posts 22A, 22B and scaffold building screw 104, and can afford an anchoring point for securing comminuted humeral head portion P to scaffold building posts 22A, 22B and scaffold building screw 104.

FIGS. 10-16 depict other suture anchors for attaching suture 122 to scaffold building posts 22A, 22B and scaffold building screw 104, and, in doing so, securing comminuted humeral head portion P in position relative to scaffold building posts 22A, 22B and scaffold building screw 104.

Figure 10:
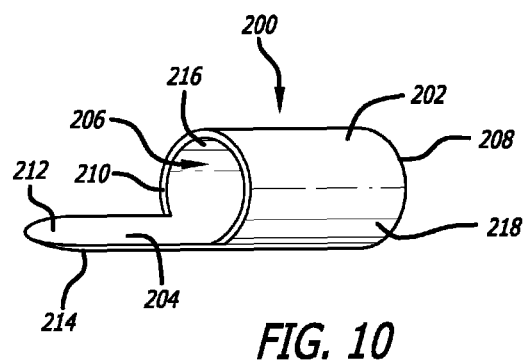
FIG. 10 is a perspective view of another suture anchor for use as part of the fracture fixation systems disclosed herein.
Figure 11:
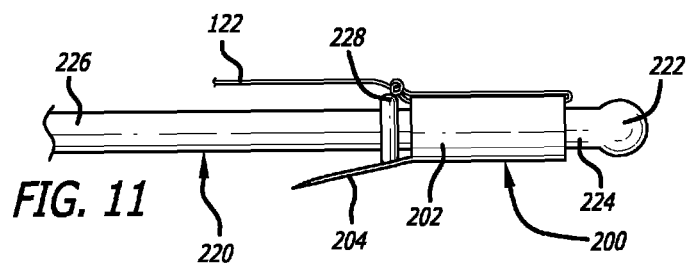
FIG. 11 is a side elevational view of the suture anchor depicted in FIG. 10 with a suture attached thereto and a complementary insertion tool inserted therethrough.
Figure 12:
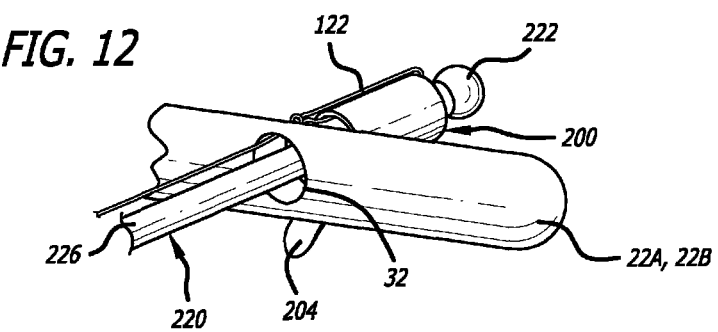
FIG. 12 is a perspective view of the suture anchor and the insertion tool depicted in FIG. 11 being inserted through a scaffold building post of the fracture fixation system depicted in FIG. 1.

FIGS. 10-12 depict a suture anchor 200 having a body portion 202 and a leg portion 204 extending outwardly from body portion 202. Body portion 202 is generally cylindrical, and includes an opening 206 therethrough extending between a first end 208 and a second end 210. As depicted in FIGS. 10-12, leg portion 204 extends outwardly from body portion 202 at second end 210, and leg portion 204 includes a first surface 212 and a second surface 214. First and second surfaces 212 and 214 are continuous with an interior surface 216 and an exterior surface 218, respectively, of body portion 202. Body portion 202 and leg portion 204 can be made of a resilient material such as nitinol to afford movement of leg portion 204 relative to body portion 202.

Suture anchor 200 and suture 122 attached thereto can be received through bracing apertures 32, 34, and 112, of scaffold building posts 22A, 22B and scaffold building screw 104, respectively. For example, as depicted in FIG. 12, one of scaffold building posts 22A, 22B is depicted with suture anchor 200 (and suture 122 attached thereto) inserted through the corresponding one of bracing apertures 32. As depicted in FIG. 12, leg portion 204 serves as a catch to prevent withdrawal of suture anchor 200 through bracing apertures 32, 34, and 112. Thus, when suture 122 is attached to suture anchor 200, suture anchor 200 can serve in attaching suture 122 to scaffold building posts 22A, 22B and scaffold building screw 104, and can afford an anchoring point for securing comminuted humeral head portion P to scaffold building posts 22A, 22B and scaffold building screw 104.

Insertion tool 220 can be used to facilitate insertion of suture anchor 200 through bracing apertures 32, 34, and 112. Insertion tool 220 includes an end portion 222, a first shaft portion 224, a second shaft portion 226, and a shoulder 228 between first and second shaft portions 226. End portion 222, as depicted in FIGS. 10-12 can be spherical and is sized to afford passage through opening 206 of body portion 202. Shoulder 228 is sized to prevent axial movement of suture anchor 200 along insertion tool 220.

To insert suture anchor 200 and suture 122 through bracing apertures 32, 34, and 112, suture anchor 200 is slipped over end portion 222 to reside between end portion 222 and shoulder portion 228 on first shaft portion 224. Suture 122 can be attached to suture anchor 200 before or after receipt of suture anchor 200 on insertion tool 220. As depicted in FIG. 11, shoulder 228 is sized to prevent suture anchor 200 from moving from first shaft portion 224 to second shaft portion 226. Thereafter, suture anchor 200 is inserted into an entrance of and completely through one of bracing apertures 32, 34, and 112 using insertion tool 220. Once leg portion 204 exits through the one of bracing apertures 32, 34, and 112, insertion tool 220 can be retracted through opening 208 and through the one of bracing apertures 32, 34, and 112. Leg portion 204 serves to prevent withdrawal of suture anchor 200 through the one of bracing apertures 32, 34, and 112. As such, suture 122 is secured to scaffold building posts 22A, 22B and scaffold building screw 104 corresponding to the one of bracing apertures 32, 34, and 112 when anchor 200 is inserted completely therethrough.

Figure 13:
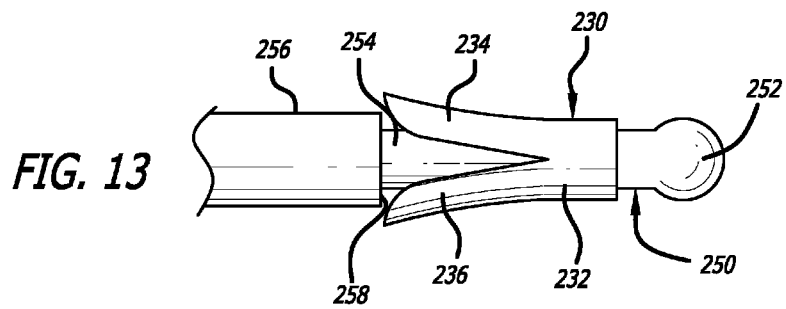
FIG. 13 is a side elevational view of yet another suture anchor for use as part of the fracture fixation systems disclosed herein with a complementary insertion tool.
Figure 14:
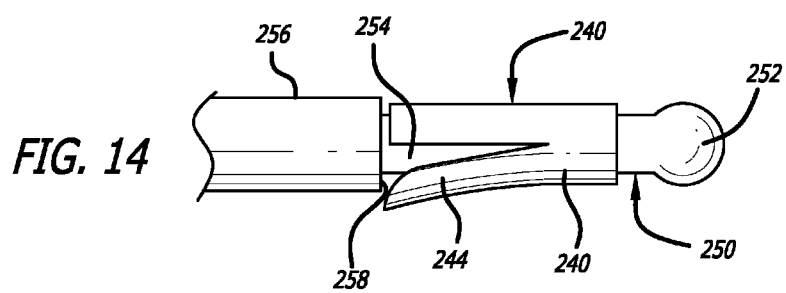
FIG. 14 is a side elevational view of yet another suture anchor for use as part of the fracture fixation systems disclosed herein with a complementary insertion tool.

FIGS. 13 and 14 depict suture anchors 230 and 240 used in association with an insertion tool 250. Suture anchors 230 and 240 are similar in function to suture anchor 200, and also can be made of a resilient material such as nitinol. However, rather than using leg portion 204 as a catch for resisting withdrawal from bracing apertures 32, 34, and 112, the bodies of suture anchors 230 and 240 are configured for resisting such withdrawal. For example, as depicted in FIG. 13, suture anchor 230 includes a body 232 having a first flared portion 234 and a second flared portion 236 that serve as catches. Furthermore, as depicted in FIG. 14, suture anchor 240 includes a body 242 having a single flared portion 244 that serves as a catch. When suture 122 is attached to suture anchors 230 and 240, and suture anchors 230 and 240 are inserted through bracing apertures 32, 34, and 112, first and second flared portions 234 and 236 (of suture anchor 230) and single flared portion 244 (of suture anchor 240) prevent withdrawal thereof to secure suture 122 to scaffold building posts 22A, 22B and scaffold building screw 104.

As depicted in FIGS. 13, and 14, insertion tool 250 is also similar in function to insertion tool 220. However, rather than using shoulder portion 228 to prevent movement from first shaft portion 224 to second shaft portion 226, insertion tool 250 includes an end portion 252, a first shaft portion 254, and a second shaft portion 256, where second shaft portion 256 is larger than first shaft portion 254 to prevent such movement. Thus, a shoulder 258 is naturally formed at insertion of first and second shaft portions 254 and 256. Shoulder 258 prevents axial movement of suture anchors 230 and 240 along insertion tool 250.

Figure 15:
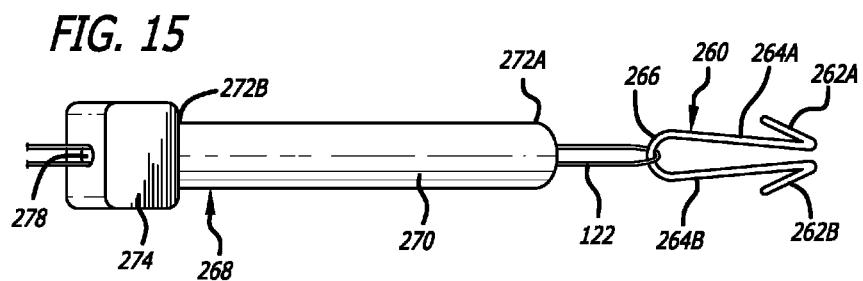
FIG. 15 is a perspective view of a further suture anchor for use as part of the fracture fixation systems disclosed herein with a complementary insertion tool.
Figure 16:
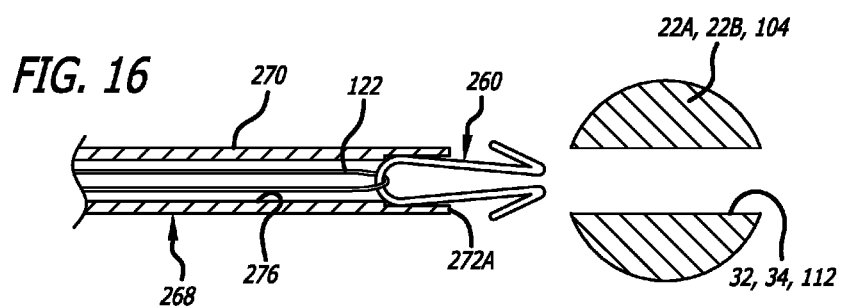
FIG. 16 is a side cross-sectional view of the suture anchor and the insertion tool depicted in FIG. 15 being inserted into the scaffold building post or scaffold building screw of the fracture fixation systems depicted in FIGS. 1 and 2.

FIGS. 15 and 16 depict a suture anchor 260 and an insertion tool 268. Suture anchor 260, in similar fashion to suture anchors 160, 200, 230, and 240, can serve in attaching suture 122 to scaffold building posts 22A, 22B and scaffold building screw 104, and can afford an anchoring point for securing comminuted humeral head portion P to scaffold building posts 22A, 22B and scaffold building screw 104.

Suture anchor 260 is generally arrow shaped, and includes a first arm portion 262A, a second arm portion 262B, a first body portion 264A, a second body portion 264B, and a connecting portion 266 between first and second body portions 264A and 264B. As discussed below, first and second arm portions 262A and 262B serve as catches for resisting withdrawal from openings such as bracing apertures 32, 34, and 112.

As depicted in FIGS. 15 and 16, first arm portion 262A forms a first acute angle with respect to first leg portion 264A, and second arm portion 262B forms a second acute angle with respect to second leg portion 264B. Furthermore, first and second body portions 264A and 264B, and connecting portion 266 together form a generally U-shaped structure that serves as a cavity for receiving suture 122 therethrough. In similar fashion to slot 168 of suture anchor 160, suture 122 can be looped around or tied to suture anchor 260 using the cavity formed by first and second body portions 264A and 264B, and connecting portion 266.

Suture anchor 260 can be made of a resilient material such as nitinol. Thus, while suture anchor 260 is biased in the position depicted in FIGS. 15 and 16, suture anchor 260 can be contracted and expanded. That is, first and second body portions 264A and 264B are moveable toward one another under compression (i.e., contraction thereof) and moveable away from one another under tension (i.e., expansion thereof). For example, first and second body portions 264A and 264B at the connections thereof with first and second arm portions 262A and 262B, respectively, can be moved toward one another during contraction and can be moved away from one another during expansion. Furthermore, first and second arm portions 262A and 262B can be pivotable relative to first and second body portions 264A and 264B, respectively.

Suture anchor 260 can be inserted through bracing apertures 32, 34, and 112 using an insertion tool 268. Insertion tool 268 includes a shaft portion 270 (having a distal end 272A and a proximal end 272B) and a handle portion 274. Shaft portion 270 and handle portion 274 include openings 276 and 278, respectively, extending therethrough. Opening 276 in shaft portion 270 is sized to receive at least a portion of suture anchor 260 therein (FIG. 16), and opening 278 in handle portion 274 is sized to receive the suture therethrough.

To insert suture anchor 260 and suture 122 through bracing apertures 32, 34, and 112, suture 122 is first inserted through opening 276 (in shaft portion 270) and opening 278 (in handle portion 274), and then suture 122 is looped around connecting portion 266 of suture anchor 260. Thereafter, at least a portion of suture anchor 260 is received in opening 276 at distal end 272A of shaft portion 270. For example, as depicted in FIG.

16, connecting portion 266 and portions of first and second body portions 264A and 264B are received in opening 276. To afford receipt of suture anchor 260 therein, opening 276 at distal end 272A of shaft portion 270 can be sized larger (FIG. 16) than the remainder thereof, and, if necessary, suture anchor 260 can be contracted in order to facilitate receipt thereof in opening 276. Thereafter, suture anchor 260 can be inserted into an entrance of one of bracing apertures 32, 34, and 112.

Once first and second arm portions 262A and 262B exit through the one of bracing apertures 32, 34, and 112, first and second arm portions 262A and 262B expand to approximate the original shape thereof, and insertion tool 268 can be retracted though the one of bracing apertures 32, 34, and 112. First and second arm portions 262A and 262B then serve in preventing withdrawal of suture anchor 260 from the one of bracing apertures 32, 34, and 112 through which it has been inserted. That is, if suture 122 attached to suture anchor 260 is tensioned (e.g., in an attempt to withdrawal suture anchor 260 from the one of bracing apertures 32, 34, and 112), contact of first and second arm portions 262A and 262B with portions of the corresponding one of scaffold building posts 22A, 22B and scaffold building screw 104 adjacent the exit of bracing apertures 32, 34, and 122 forces first and second arm portions 262A and 262B to pivot away from first and second leg portions 264A and 264B, respectively. In doing so, the first acute angle between first arm portion 262A and first leg portion 264A increases, and the second acute angle between second arm portion 262B and second leg portion 264B increases. However, while the first and second acute angles increase, the first and second angles do not increase enough so that the first and second angles are greater than 90-100°. As such, first and second arm portions 262A and 262B serve as a catches to prevent withdrawal of suture anchor 200 through bracing apertures 32, 34, and 112, thereby attaching suture 122 to the corresponding one of scaffold building posts 22A, 22B and scaffold building screw 104.

Like suture anchor 160, suture anchor 260 can be used in conjunction with hollow needle 180, and can be inserted through soft tissues and/or bone using hollow needle 180. Furthermore, suture anchor 160 can be used with insertion tool 268 (in similar fashion to use with suture anchor 260) to facilitate insertion of suture anchor 160 through bracing apertures 32, 34, and 112.

While suture anchors 130, 142, 144, 160, 200, 230, 240, and 260 are discussed in association with bracing apertures 32, 34, and 112, use of suture anchors 130, 142, 144, 160, 200, 230, 240, and 260 is not limited thereto. Suture anchors 130, 142, 144, 160, 200, 230, 240, and 260 can be used in conjunction with the other illustrative embodiments of the fracture fixation system described herein and other structures provided for use with the illustrative embodiments. For example, structures (such as projections, protrusions, protuberances, etc.) can extend outwardly from scaffold building posts 22A, 22B, scaffold building screw 104, plate portions 12 and 102, and/or other components of the illustrative embodiments of the fracture fixation system described herein. Furthermore, the structures can be indentations and associated latches or hooks formed in scaffold building posts 22A, 22B, scaffold building screw 104, plate portions 12 and 102, and/or other components of the illustrative embodiments of the fracture fixation system described herein. Such structures could be configured to capture, hold, or otherwise retain suture anchors 130, 142, 144, 160, 200, 230, 240, and 260. Furthermore, such structures could be configured for wrapping suture 122 therearound, or otherwise securing suture 122 thereto (without use of suture anchors 130, 142, 144, 160, 200, 230, 240, and 260). Additionally, suture anchors 142, 144, 160, 200, 230, 240, and 260 can also be used in conjunction with anchor post 130. For example, anchor post 130 could be received in the bracing apertures described herein (e.g., one of bracing apertures 32, 34, and 112), and suture anchors 142, 144, 160, 200, 230, 240, and 260 could be received through eyelet portion 136 to secure suture 122 thereto.

Figure 17:
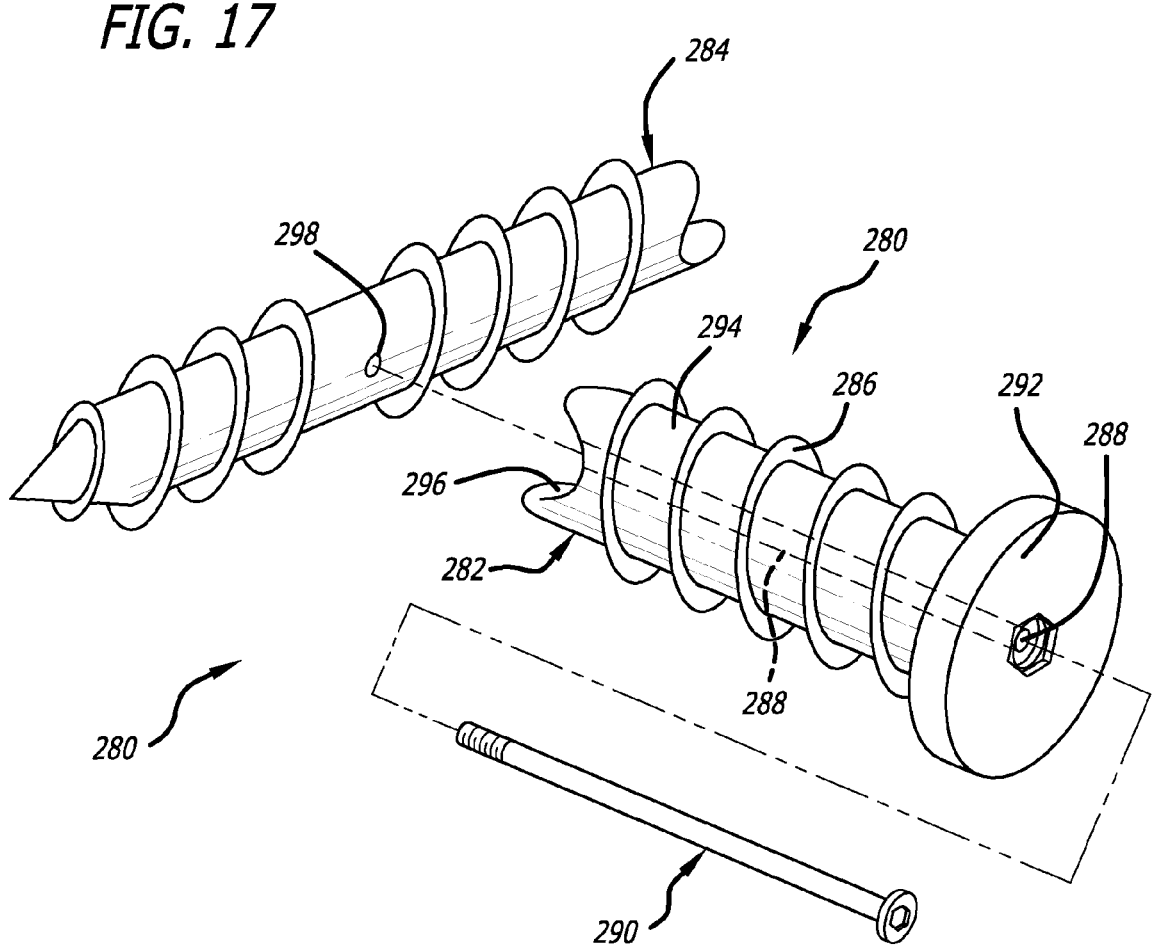
FIG. 17 is a perspective view of a third embodiment of the fracture fixation system.

In addition, another illustrative embodiment of a fracture fixation system is generally indicated by the numeral 280 in FIG. 17. Fracture fixation system 280 includes a scaffold building screw 282 for insertion through a plate portion (not shown) into a bony structure to interface with a cross member 284. Fracture fixation system 280 can be used with fracture fixation systems 10 and 100, and with suture anchors 130, 142, 144, 160, 200, 230, 240, and 260. To that end, scaffold building screw 282 can be used with external plate portions 12 and 102, and can include one or more bracing apertures (not shown) for receiving suture anchors 130, 142, 144, 160, 200, 230, 240, and 260.

Scaffold building screw 282 includes threads 286 to facilitate attachment to the bony structure. Scaffold building screw 282 includes a channel 288 extending therethrough (between the proximal and distal ends) adapted to receive a set screw 290, and includes a head 292, a shaft 294, and a concavity 296 opposite head 292.

Once scaffold building screw 282 is positioned in the bony structure, cross member 284 is also inserted into the bony structure. Cross member 284 is inserted transversely relative to scaffold building screw 282 to contact concavity 296. Cross member 284 can be threaded or non-threaded, and is sized to be received in concavity 296. Cross member 284 includes a threaded aperture 298 that can be aligned with channel 288. Thus, when channel 288 and threaded aperture 298 are aligned with one another, set screw 290 can be inserted through channel 288 into threaded aperture 298. Engagement of set screw 290 with threaded aperture 298 secures cross member 284 in position relative to scaffold building screw 282. In doing so, cross member 284 can be rigidly secured to scaffold building screw 282.

A guide member (not shown) can be used to facilitate alignment of scaffold building screw 282 and cross member 284. For example, the guide member can be positioned relative to scaffold building screw 282 and/or the plate portion (e.g., the external plate portions 12 and 102) receiving scaffold building screw 282 to insure proper positioning of cross member 284. Furthermore, a portion (e.g., head 292) of scaffold building screw 282 and/or a portion of cross member 284 can include an indicia to afford the proper orientation thereof to facilitate receipt of cross member 284 in concavity 296 and alignment of channel 288 and threaded aperture 298.

FIGS. 18-26 depict further illustrative embodiments of fracture fixation systems generally indicated by the numerals 300, 400, 420, 440, 460, 480, 500, and 540. Fracture fixation systems depicted in FIGS. 18-26 can be used with fracture fixation systems 10, 100, and 280, and with suture anchors 130, 142, 144, 160, 200, 230, 240, and 260. As such, bracing apertures associated with fixation systems 300, 400, 420, 440, 460, 480, 500, and 540 can be configured for receipt of suture anchors 130, 142, 144, 160, 200, 230, 240, and 260.

Figure 18:
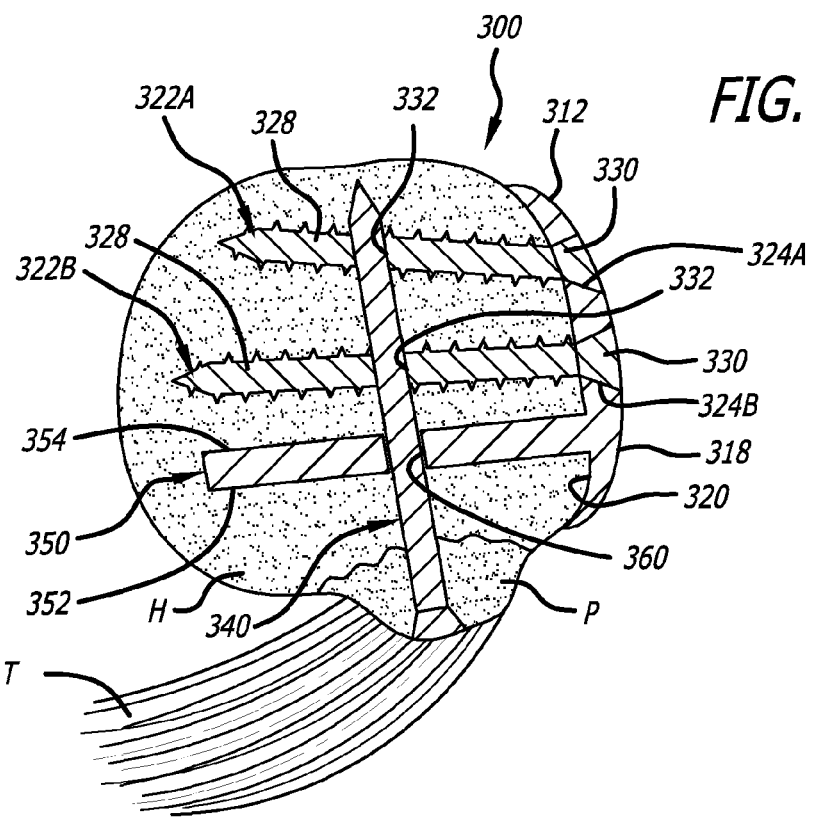
FIG. 18 is a top cross-sectional view of a fourth embodiment of the fracture fixation system positioned with respect to a repaired humeral head.
Figure 19:
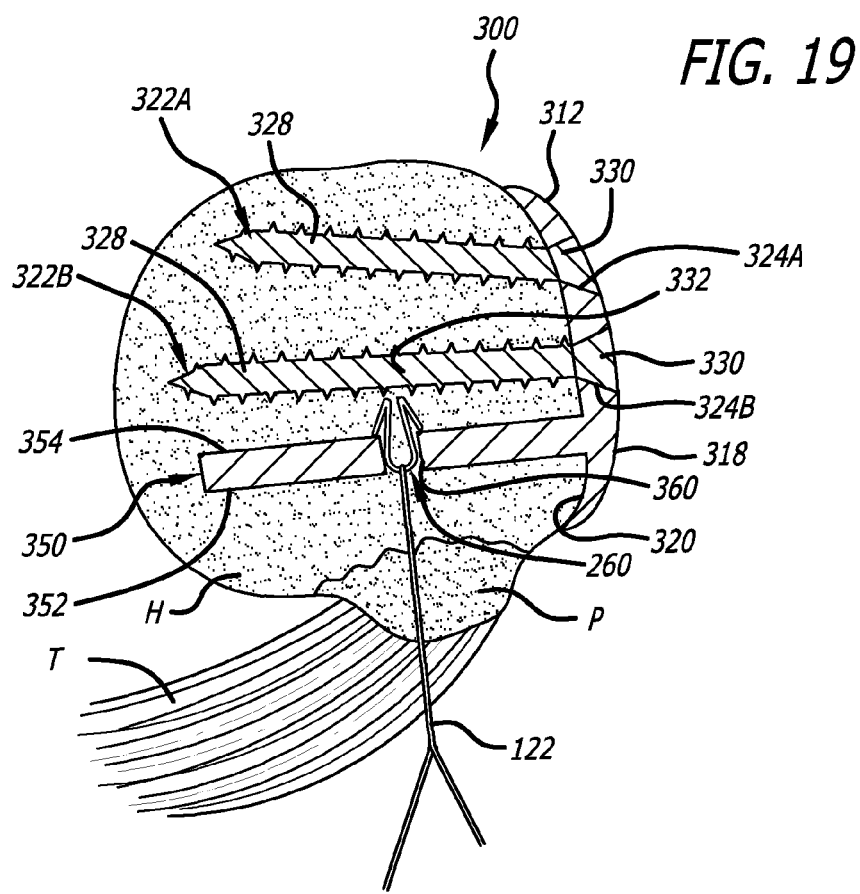
FIG. 19 is a top cross-sectional view of the fourth embodiment of the fracture fixation system depicted in FIG. 18 in use with the suture anchor depicted in FIGS. 15 and 16.

FIGS. 18 and 19 depict an illustrative embodiment of fracture fixation system generally indicated by the numeral 300. Fracture fixation system 300 includes an external plate portion 312 similar to external plate portions 12 and 102 of fracture fixation systems 10 and 100, respectively. External plate portion 312 can be elongated to afford attachment to humeral shaft portion 16 of humeral bone H (depicted in FIGS. 1 and 2) in similar fashion to external plate portions 12 and 102.

External plate portion 312 includes an upper surface 318 and a lower surface 320, and, as depicted in FIGS. 18 and 19, lower surface 320 can be contoured to the shape of portions of humeral bone H. For example, portions of lower surface 320 can be contoured to the shape of portions of comminuted humeral head, and other portions of lower surface 320 can be contoured to the shape of humeral shaft portion 16.

External plate portion 312 can include screw apertures (not shown) for attaching external plate portion 312 to humeral bone H using plate screws (not shown) in similar fashion to fracture fixation systems 10 and 100. The screw apertures for receiving the plate screws extend between upper surface 318 and lower surface 320, and can be provided along the length of external plate portion 312. As such, the screw apertures and the plate screws received therein can be used to attach external plate portion 312 to the external surfaces of humeral shaft portion 16. Furthermore, depending on whether additional portions of the comminuted humeral head remain attached to humeral shaft portion 16, external plate portion 12 can also be attached to the exterior surfaces thereof using the plate screws.

Like fracture fixation systems 10 and 100, fracture fixation system 300 also can include attachment structures in the form of one or more scaffold building posts and/or screws for facilitating attachment of comminuted humeral head portion P. As depicted in FIGS. 18 and 19, fracture fixation system 300 includes two scaffold building posts 322A and 322B received in scaffold building post apertures 324A and 324B. As depicted in FIGS. 18 and 19, scaffold building posts 322A and 322B can be secured relative to external plate portion 312.

Scaffold building posts 322A and 322B each include a shaft 328 and a head 330. Shaft 328 can be provided with threads (not shown) to facilitate attachment thereof to larger portions of the comminuted humeral head. If necessary, scaffold building posts 322A and 322B can be locked to scaffold building post apertures 324A and 324B, respectively, using cooperating threads (not shown) on exterior of heads 330 and on the interior of scaffold building post apertures 324A and 324B.

Scaffold building posts 322A and 322B can be provided with or without fenestrations. If no fenestrations are provided, sutures, wires, and/or cables can be wrapped around scaffold building posts 322A and 322B to facilitate attachment of comminuted humeral head portion P thereto. Furthermore, if fenestrations are provided, shafts 328 of scaffold building posts 322A and 322B can include one or more bracing apertures 332 formed therethrough. As depicted in FIG. 18, scaffold building posts 322A and 322B each include one of bracing apertures 332. As discussed below, bracing apertures 332 can receive a cross member 340 or can receive sutures, wires, cables, and/or suture anchors. Moreover, fenestrations (not shown) can also be provided in cross member 340, and the fenestrations in cross member 340 can also receive sutures, wires, cables, and/or suture anchors.

Bracing apertures 332 can extend transversely through shafts 328 of each of scaffold building posts 322A and 322B. Bracing apertures 332 may be disposed in a generally perpendicular relationship or at any desired angle with respect to the longitudinal axes of shafts 328. Moreover, if multiple bracing apertures 332 are provided in one of shafts 328, the multiple bracing apertures 332 may be disposed in generally perpendicular or transverse relationships with respect to each other.

In addition to the attachment structures in the form of scaffold building posts 322A and 322B, as depicted in FIGS. 18 and 19, fracture fixation system 300 includes a fin 350 extending outwardly from lower surface 320. Fin 350 and fins of other illustrative embodiments of the fracture fixation system disclosed herein can be plate-like projections having various shapes and dimensions, and apertures can be provided in fin 350 and the other fins for receiving cross members, sutures (such as suture 122), wires, cables, and/or suture anchors (such as suture anchors 130, 142, 144, 160, 200, 230, 240, and 260).

As depicted in FIGS. 18 and 19, fin 350 includes a first side 352, a second side 354, a length measured outwardly from lower surface 320, and a thickness perpendicular to the length. The width of fin 350 is perpendicular to the length and the thickness thereof, and, because the width of fin 350 is aligned with the length of external plate portion 312, is not shown in FIGS. 18 and 19. As discussed below, the position, number, angles, and curvature of the fin or fins can be varied in association with fracture fixation systems 300, 400, 420, 440, 460, and 480. Regarding position, fin 350 and fins of other illustrative embodiments of the fracture fixation system disclosed herein, for example, can be positioned proximate the center of exterior plate portion 312, proximate one or more edges of exterior plate portion 312, or anywhere therebetween.

Fin 350 can include one or more bracing apertures 360 formed therethrough extending between first and second sides 352 and 354. As depicted in FIGS. 18 and 19, fin 350 includes one of bracing apertures 360. Furthermore, like bracing apertures 332 formed in scaffold building posts 322A and 322B, bracing aperture 360 can receive cross member 340 therethrough or can receive sutures, wires, cables, and/or suture anchors.

As depicted in FIG. 18, when using cross member 340, bracing apertures 332 and bracing apertures 360 can be aligned with one another to afford passage of cross member 340 through scaffold building posts 322A and 322B, and fin 350. Cross member 340 can be connected to scaffold building posts 322A and 322B, and fin 350, and can be used to attach comminuted humeral head portion P to fin 350, and hence, to other portions of humeral bone H. Furthermore, bracing apertures 332 (of scaffold building posts 322A and 322B) and bracing apertures 360 (of fin 350) can be threaded to engage complementary threads provided on the cross member 340 to strengthen the connection therebetween.

When using sutures, wires, cables, and/or suture anchors, suture anchor 260 (and an attached suture, wire, or cable) can be received through bracing aperture 360 to facilitate attachment of comminuted humeral head portion P to fin 350, and hence, to other portions of humeral bone H. For example, as depicted in FIG. 19, suture anchor 260 is attached to suture 122, and comminuted humeral head portion P is being attached to fin 350 using suture 122 and suture anchor 260. Furthermore, the sutures, wires, cables, and/or suture anchors can be used to secure associated tissue T to comminuted humeral head portion P and other portions of humeral bone H.

While not depicted in FIG. 19, scaffold building posts 322A and 322B can include bracing apertures 332 aligned with bracing aperture 360. As such, in addition to bracing aperture 360, suture 122 and suture anchor 260 attached thereto could be received through bracing apertures 332 (not shown in FIG. 19) formed in scaffold building posts 322A and 322B. Furthermore, in similar fashion to fixation systems 10 and 100, one of scaffold building posts 322A and 322B could be rotated to reposition bracing apertures 332 formed therein rotationally and wind suture 122 around shaft 328. That is, one of scaffold building posts 322A and 322B could be rotated so long as attachment of suture 122 and suture anchor 260 to fin 350 and/or the other of scaffold building posts 322A and 322B does interfere with such rotation. Such rotation would draw comminuted humeral head portion P toward fin 350 and scaffold building posts 322A, 322B.

Figure 20:
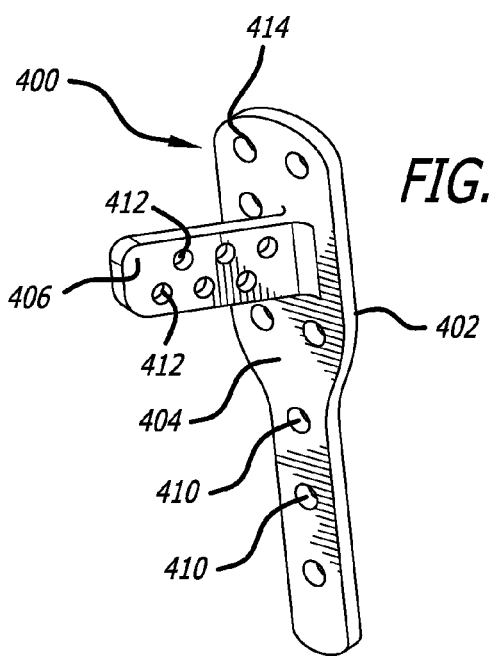
FIG. 20 is a perspective view of a fifth embodiment of the fracture fixation system.
Figure 21:
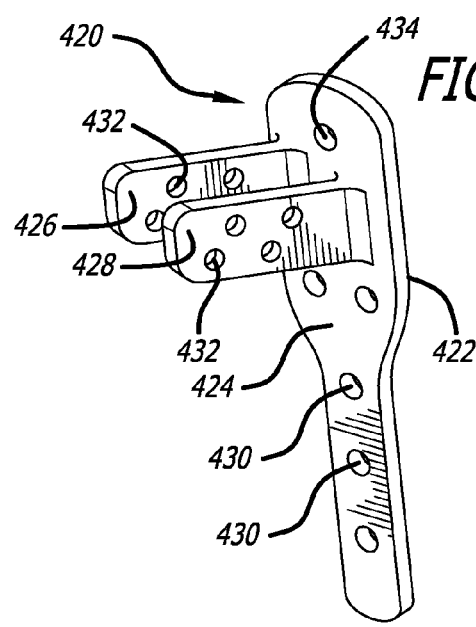
FIG. 21 is a perspective view of a sixth embodiment of the fracture fixation system.
Figure 22:
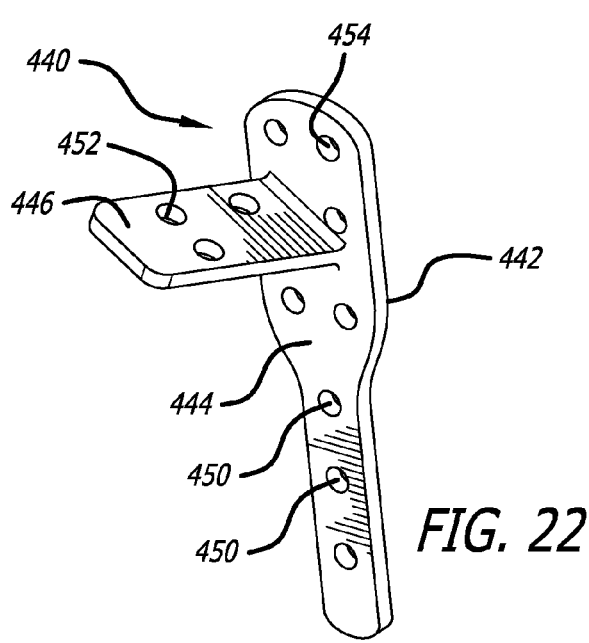
FIG. 22 is a perspective view of a seventh embodiment of the fracture fixation system.

Illustrative embodiments 400, 420, and 440 of the fracture fixation system disclosed herein are depicted in FIGS. 20-22, respectively. Fracture fixation system 400 depicted in FIG. 20 includes an exterior plate portion 402 having a lower surface 404 and a single fin 406 extending outwardly from lower surface 404—the width of fin 406 is aligned with the longitudinal axis (or along the length) of exterior plate portion 402. Fracture fixation system 420 depicted in FIG. 21 includes an exterior plate portion 422 having a lower surface 424 and two fins 426 and 428 extending outwardly from lower surface 424—fins 426 and 428 are spaced apart from one another and the widths of fins 426 and 428 are aligned with the longitudinal axis (or along the length) of exterior plate portion 422. Fracture fixation system 440 depicted in FIG. 22 includes an exterior plate portion 442 having a lower surface 444 and a single fin 446—the width of fin 446 is oriented transversely to the longitudinal axis (or across the longitudinal axis) of exterior plate portion 442.

As depicted in FIGS. 20-22, exterior plate portions 402, 422, and 442 can include screw apertures 410, 430, and 450, respectively, spaced therealong for receiving plate screws (not shown) therethrough. The plate screws can be used to attach exterior plate portions 402, 422, and 442 to the external surface of humeral shaft portion 16. Furthermore, depending on whether additional portions of the comminuted humeral head remain attached to humeral shaft portion 16, external plate portions 402, 422, and 442 can also be attached to the exterior surfaces thereof using the plate screws. Like lower surface 320 of exterior plate portion 312 of fracture fixation system 300, portions of lower surfaces 404, 424, and 444 of exterior plate portions 402, 422, and 442, respectively, can be contoured to portions of the comminuted humeral head, and other portions of lower surfaces 404, 424, and 444 can be contoured to the shape of humeral shaft portion 16.

Like fin 350 of fracture fixation 300, fin 406, fins 426 and 428, and fin 446 can include bracing apertures 412, 432, and 452, respectively, for receiving cross members, sutures, wires, cables, and/or suture anchors. Furthermore, exterior plate portions 402, 422, and 442 can include apertures 414, 434, and 454 for receiving scaffold building posts (not shown) and/or scaffold building screws (not shown). The scaffold building posts and/or scaffold building screws of the fracture fixation systems 400, 420, and 440 can also include apertures (not shown) for receiving cross members, sutures, wires, cables, and/or suture anchors. As such, the cross members, sutures, wires, cables, and/or suture anchors can be received through bracing apertures 412, 432, and 452 and corresponding apertures formed in the scaffold building posts and/or scaffold building screws of fracture fixation systems 400, 420, and 440.

Figure 23:
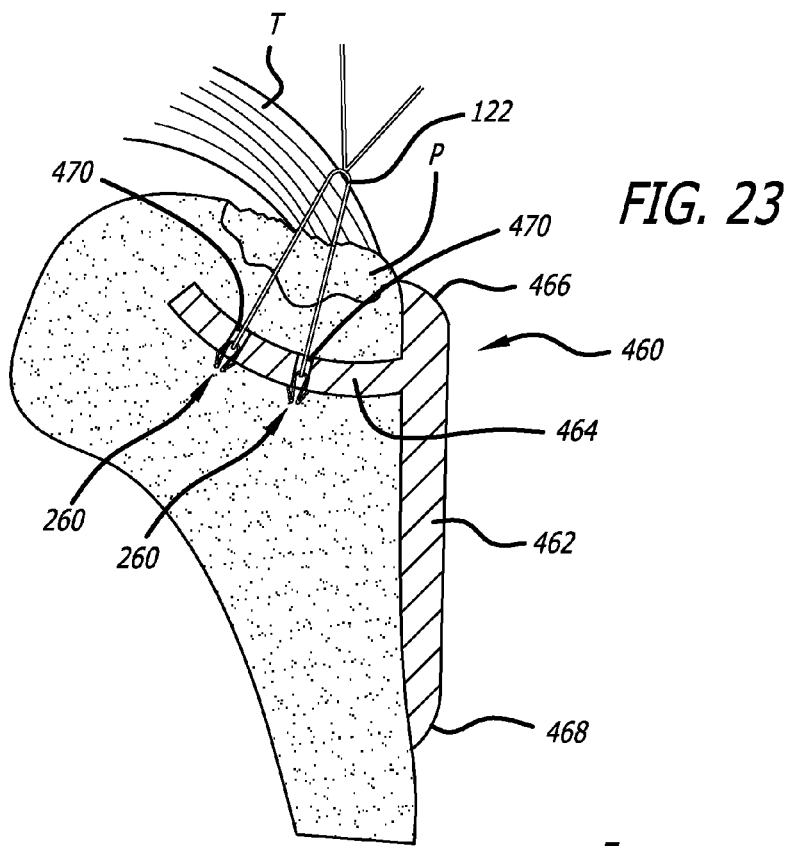
FIG. 23 is a side cross-sectional view of an eighth embodiment of the fracture fixation system positioned with respect to a repaired humeral head.
Figure 24:
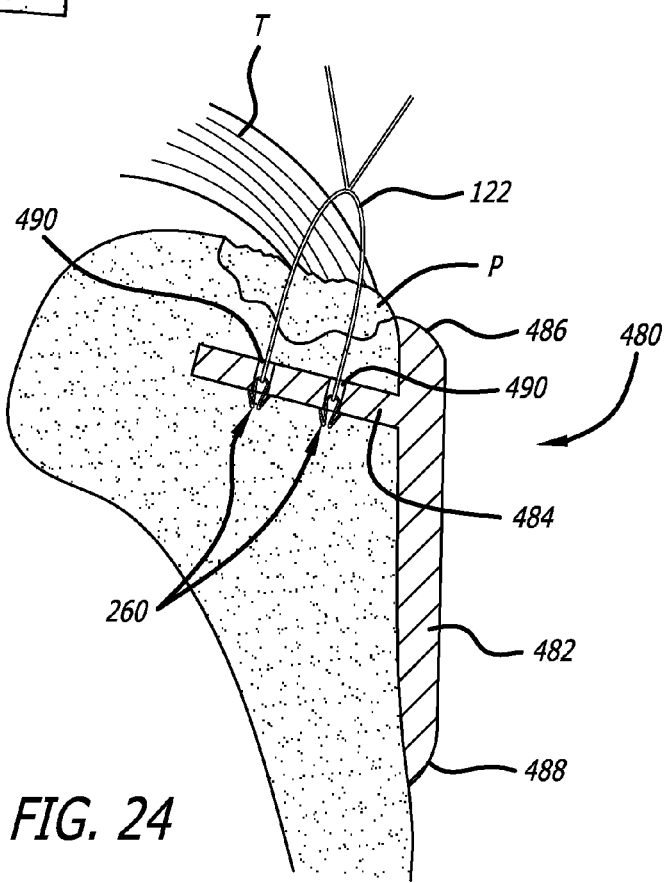
FIG. 24 is a side cross-sectional view of a ninth embodiment of the fracture fixation system positioned with respect to a repaired humeral head.

Illustrative embodiments 460 and 480 of the fracture fixation system disclosed herein are depicted in FIGS. 23 and 24, respectively. Fracture fixation systems 460 and 480 can incorporate the features of fracture fixation systems 300, 400, 420, and 440, and, as depicted in FIGS. 23 and 24 include exterior plate portions 462 and 482, respectively. Fracture fixation system 460 includes a fin 464, a first end 466, and a second end 468, and fin 464 is both oriented transversely to the longitudinal axis (or across the longitudinal axis) of exterior plate portion 462, and curved toward first end 466; and fracture fixation system 480 includes a fin 484, a first end 486, and a second end 488, and fin 484 is both oriented transversely to the longitudinal axis (or across the longitudinal axis) of exterior plate portion 482, and angled toward first end 486.

While fins 464 and 484 are depicted as being curved and angled, respectively, toward first ends 466 and 486 in FIGS. 23 and 24, fins 464 and 484 can also be curved and angled toward second ends 468 and 488. Moreover, the curvature and angles of fins 464 and 484, respectively, can be varied, and the transverse orientation of fins 464 and 484 relative to the longitudinal axes of exterior plate portions 462 and 482, respectively, can also be varied. Furthermore, multiple fins 464 and 484 can be provided in association with fracture fixation systems 460 and 480. Fins 464 and 484 can include apertures 470 and 490, respectively, for receiving cross members, sutures, wires, cables, and/or suture anchors. For example, as depicted in FIGS. 23 and 24, comminuted humeral head portion P is being secured to fins 464 and 484, respectively, using suture 122 and suture anchors 260 received through apertures 470 and 490.

Figure 25:
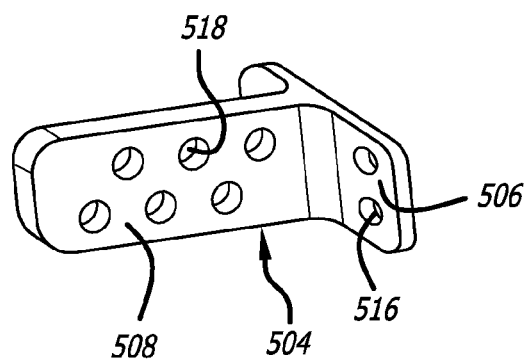
FIG. 25 is an enlarged perspective view of a fin element of a tenth embodiment of the fracture fixation system.
Figure 26:
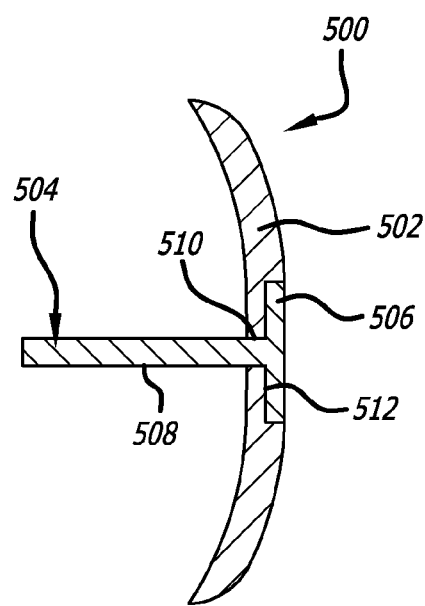
FIG. 26 is a top cross-section view of the tenth embodiment of the fracture fixation system.
Figure 27:
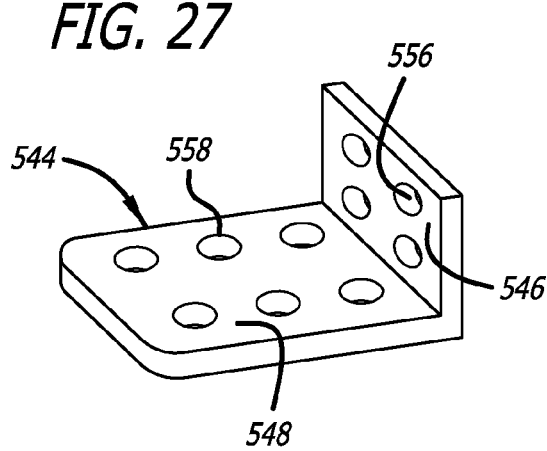
FIG. 27 is an enlarged perspective view of a fin element of an eleventh embodiment of the fracture fixation system.
Figure 28:
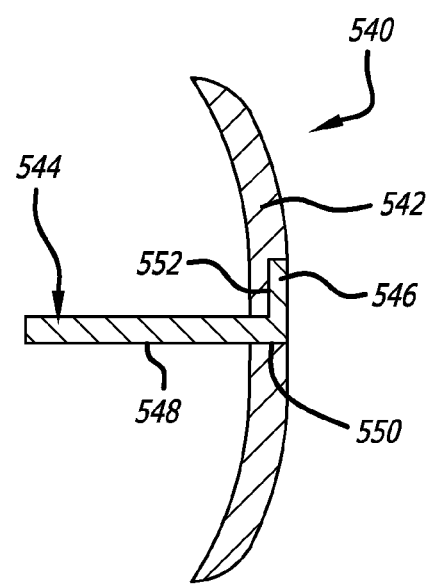
FIG. 28 is a top cross-section view of the eleventh embodiment of the fracture fixation system.

Illustrative embodiment 500 of the fracture fixation system disclosed herein is depicted in FIGS. 25 and 26, and illustrative embodiment 540 of the fracture fixation system disclosed herein is depicted in FIGS. 27 and 28. Fracture fixation systems 500 and 540 can incorporate the features of fracture fixation systems 300, 400, 420, 440, 460, and 480.

Fracture fixation system 500 depicted in FIG. 26 includes an exterior plate portion 502 and a fin element 504 (FIGS. 25 and 26) shaped as a "T" attached to exterior plate portion 502. Fin element 504 includes a base portion 506 and an extension portion 508 extending outwardly from base portion 506. In addition to apertures (not shown) for receiving plate screws and/or scaffold building screws (not shown), exterior plate portion 502 includes a slot 510 and a groove (or retaining recess) 512 formed therein. Slot 510 is sized to receive extension portion 508 therethrough, and groove 512 is sized to receive base portion 506 therein. When assembled, extension portion 508 extends outwardly from exterior plate portion 502, and base portion 506 is nested in groove 512. To attach fin element 504 to exterior plate portion 502, screws (not shown) can be inserted through apertures 516 formed through base portion 506 and received in corresponding apertures (not shown) formed in exterior plate portion 502. Like the fins 350, 406, 426, 428, 446, 464, and 484, extension portion 508 can include bracing apertures 518 formed therethrough for receiving cross members, sutures, wires, cables, and suture anchors.

Fracture fixation system 540 depicted in FIG. 28 includes an exterior plate portion 542 and a fin element 544 (FIGS. 27 and 28) shaped as an "L" attached to exterior plate portion 542. Fin element 544 includes a base portion 546 and an extension portion 548 extending outwardly from base portion 546. In addition to apertures (not shown) for receiving plate screws and/or scaffold building posts (not shown), exterior plate portion 542 includes a slot 550 and a groove (or retaining recess) 552 formed therein. Slot 550 is sized to receive extension portion 548 therein. When assembled, extension portion 548 extends outwardly from exterior plate portion 542, and base portion 546 is nested in groove 552. To attach fin element 544 to exterior plate portion 542, screws (not shown) can be inserted through apertures 556 formed through base portion 546 and received in corresponding apertures (not shown) in exterior plate portion 542. Like fins 350, 406, 426, 428, 446, 464, and 484, extension portion 548 can include bracing apertures 558 formed therethrough for receiving cross members, sutures, wires, cables, and suture anchors.

Furthermore, while fin elements 504 and 544 have "T" and "L" shapes, respectively, extension portions 508 and 548 can also be curved, angled, and oriented in similar fashion to fins 350, 406, 426, 428, 446, 464, and 484. Furthermore, multiple fin elements 504 and 544 can be provided in association with fracture fixation systems 500 and 540.

In summary, fracture fixation systems 10, 100, 280, 300, 400, 420, 440, 460, 480, 500, and 540 facilitate repair and reattachment of the comminuted humeral head and tissue associated therewith to the remainder of humeral bone H. Furthermore, suture anchors 130, 142, 144, 160, 200, 230, 240, and 260 aid in anchoring comminuted humeral head portion P and associated tissue T to components of fracture fixation systems 10, 100, 280, 300, 400, 420, 440, 460, 480, 500, and 540, and hence, relative to one another and humeral bone H to facilitate healing. Although fracture fixation systems 10, 100, 280, 300, 400, 420, 440, 460, 480, 500, and 540 are described in association with the comminuted humeral head and the tissue associated therewith, fracture fixation systems 10, 100, 280, 280, 300, 400, 420, 440, 460, 480, 500, and 540 are not so limited. Fracture fixation systems 10, 100, and 280 can be used elsewhere in the body to repair and reattach comminuted bone portions and tissue associated therewith. Other embodiments of the invention will be apparent to those skilled in the art from consideration of the specification and practice of the invention disclosed herein. Accordingly, it is intended that the specification and examples be considered as exemplary only.

What is claimed is:

1. A method for repairing a comminuted bone including at least an unfractured bone portion and fractured bone portions, the method comprising the acts of:
    utilizing a plate having an upper surface, a lower surface opposite the upper surface, and at least one aperture for receiving one of a screw and a post therethrough;
    securing the plate to the unfractured bone portion of the comminuted bone;
    inserting the one of the screw and the post through the at least one aperture through the plate;
    attaching a portion of the fractured bone portions to the one of the screw and the post using at least one suture; and
    rotating the one of the screw and the post to wind the at least one suture around the one of the screw and the post, wherein the winding of the at least one suture draws the portion of the fractured bone portions closer to the one of the screw and the post to position the portion of the fractured bone portions relative to the unfractured bone portion;
    the winding of the at least one suture being in contact with an exterior of the one of the screw and the post and between the exterior of the one of the screw and the post and the portion of the fractured bone portions.

2. The method of claim 1, wherein the at least one suture is attached to the one of the screw and the post using a hole formed in the one of the screw and the post.

3. The method of claim 2, wherein, during rotation of the one of the screw and the post, the hole is rotated from a first position to a second position.

4. The method of claim 3, wherein the one of the screw and the post includes a mid-longitudinal axis, and the hole includes a central longitudinal axis perpendicularly aligned to the mid-longitudinal axis of the post.

5. The method of claim 1, wherein the plate is attached to the unfractured bone portion using at least one plate screw inserted through the plate and into the bone.

6. The method of claim 1, further comprising the act of utilizing a suture anchor for inhibiting withdrawal thereof from a hole formed in the one of the screw and the post, and wherein, to attach the portion of the fractured bone portions to the one of the screw and the post, the at least one suture is attached to both the suture anchor and the portion of the fractured bone portions, and the suture anchor is inserted through the hole formed in the one of the screw and the post.

7. The method of claim 1, further comprising the act of utilizing a suture anchor, and wherein the act of attaching comprises the sub-acts of attaching a first portion of the at least one suture to the suture anchor, attaching a second portion of the at least one suture to the portion of the fractured bone portions, and inserting the suture anchor and the first portion of the at least one suture at least partially through a hole formed in the one of the screw and the post, the suture anchor being configured to resist withdrawal thereof from the hole.

8. The method of claim 7, wherein the suture anchor includes a cavity for attaching the first portion of the at least one suture thereto, and at least one catch for resisting withdrawal of the suture anchor through the hole.

9. The method of claim 8, wherein the act of attaching further comprises the sub-act of contacting the at least one catch to a portion of the one of the screw and the post adjacent an exit of the hole.

10. The method of claim 7, further comprising the act of utilizing an insertion tool adapted to receive the suture anchor and the first portion of the at least one suture in an end portion thereof, and wherein the sub-act of inserting the suture anchor and the first portion of the at least one suture comprises receiving the suture anchor and the first portion of the at least one suture in the end portion of the insertion tool, inserting the end portion of the insertion tool into an entrance of and through the hole formed in the one of the screw and the post so that the at least one catch protrudes from an exit of the hole, disengaging the suture anchor and the first portion of the at least one suture from the insertion tool, and removing the insertion tool from the hole.

11. The method of claim 10, wherein the sub-act act of inserting further comprises contacting the at least one catch to a portion of the one of the screw and the post adjacent the exit of the hole to resist withdrawal through the hole.

12. The method of claim 7, further comprising the act of utilizing at least one fin extending outwardly from the lower surface of the plate, a first fin of the at least one fin including an aperture therethrough, and wherein the act of inserting one of the screw and the post further comprises the sub-act of aligning the hole of the one of the screw and the post with the aperture of the first fin, and the act of attaching further comprises the sub-act of inserting the suture anchor through the hole and the aperture.

13. The method of claim 12, wherein the plate has a longitudinal axis along the greatest dimension thereof, and the first fin has a length and a width perpendicular to the length, the length of the fin extending outwardly from the lower surface of the plate, and the width being in a plane aligned with the longitudinal axis of the plate.

14. The method of claim 12, wherein the first fin is detachable from the plate.

15. The method of claim 13, further comprising the act of utilizing a second fin having a width aligned with the width of the first fin.

16. The method of claim 7, wherein the one of the screw and the post includes a head for contacting the interior of the at least one aperture, the head and the interior each including complementary threads to prevent unwanted axial movement of the one of the screw and the post relative to the plate, and each including complementary ratchetings to prevent unwanted rotational movement of the one of the screw and the post relative to the plate.

17. A method for repairing a comminuted bone including at least an unfractured bone portion and fractured bone portions, the method comprising the acts of:
- utilizing a plate having an upper surface, a lower surface opposite the upper surface, at least one fin extending outwardly from the lower surface of the plate, and at least one aperture for receiving one of a screw and a post therethrough;
- securing the plate to the unfractured bone portion of the comminuted bone;
- inserting the one of the screw and the post through the at least one aperture through the plate;
- attaching a portion of the fractured bone portions to the one of the screw and the post using at least one suture, the at least one suture being received through an aperture formed in the at least one fin and through a hole formed in the one of the screw and the post; and
- rotating the one of the screw and the post to wind the at least one suture around the one of the screw and the post, wherein the winding of the at least one suture draws the portion of the fractured bone portions closer to the at least one fin and to the one of the screw and the post, wherein the at least one fin is positioned between the portion of the fractured bone portions and the one of the screw and the post;
- the winding of the at least one suture being in contact with an exterior of the one of the screw and the post and between the exterior of the one of the screw and the post and the portion of the fractured bone portions.

18. The method of claim 17, wherein the at least one suture is attached to the one of the screw and the post using the hole formed in the one of the screw and the post, and wherein, during rotation of the one of the screw and the post, the hole is rotated from a first position to a second position.

19. The method of claim 17, further comprising the act of utilizing a suture anchor, and wherein the act of attaching comprises the sub-acts of attaching a first portion of the at least one suture to the suture anchor, attaching a second portion of the at least one suture to the portion of the fractured bone portions, and inserting the suture anchor and the first portion of the at least one suture through the aperture formed in the at least one fin and at least partially through the hole formed in the one of the screw and the post, the suture anchor being configured to resist withdrawal thereof from the hole.

20. The method of claim 19, further comprising the act of utilizing an insertion tool adapted to receive the suture anchor and the first portion of the at least one suture in an end portion thereof, and wherein the sub-act of inserting the suture anchor and the first portion of the at one suture comprises receiving the suture anchor and the first portion of the at least one suture in the end portion of the insertion tool, inserting the end portion completely through the aperture formed in the at least one fin, inserting the end portion of the insertion tool into an entrance of and through the hole formed in the one of the screw and the post so that at least one catch formed on the suture anchor protrudes from an exit of the hole, disengaging the suture anchor and the first portion of the at least one suture from the insertion tool, and removing the insertion tool from the hole.

* * * * *